(12) United States Patent
Yokoyama et al.

(10) Patent No.: US 8,586,210 B2
(45) Date of Patent: *Nov. 19, 2013

(54) COMPOUND HAVING SUBSTITUTED ANTHRACENE RING STRUCTURE AND PYRIDOINDOLE RING STRUCTURE AND ORGANIC ELECTROLUMINESCENCE DEVICE

(75) Inventors: Norimasa Yokoyama, Ibaraki (JP); Shuichi Hayashi, Ibaraki (JP); Sawa Izumi, Tokyo (JP); Naoaki Kabasawa, Ibaraki (JP); Shigeru Kusano, Ibaraki (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 202 days.

This patent is subject to a terminal disclaimer.

(21) Appl. No.: 13/120,665

(22) PCT Filed: Sep. 18, 2009

(86) PCT No.: PCT/JP2009/066450
§ 371 (c)(1),
(2), (4) Date: Mar. 24, 2011

(87) PCT Pub. No.: WO2010/035723
PCT Pub. Date: Apr. 1, 2010

(65) Prior Publication Data
US 2011/0175079 A1 Jul. 21, 2011

(30) Foreign Application Priority Data
Sep. 24, 2008 (JP) ................................ 2008-243937

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 546/18; 546/79; 546/81; 546/101; 548/440

(58) Field of Classification Search
USPC .................. 428/690, 917; 313/504, 505, 506; 257/40, E51.032, E51.05, E51.026; 546/18, 79, 81, 101; 544/234; 548/440
See application file for complete search history.

(56) References Cited

U.S. PATENT DOCUMENTS

| | | | |
|---|---|---|---|
| 2006/0251918 A1 | 11/2006 | Iwakuma et al. | |
| 2007/0205412 A1 | 9/2007 | Bae et al. | |
| 2008/0122344 A1 | 5/2008 | Shin et al. | |
| 2010/0230660 A1* | 9/2010 | Yokoyama et al. | 257/40 |

FOREIGN PATENT DOCUMENTS

| | | |
|---|---|---|
| JP | 8 48656 | 2/1996 |
| JP | 2734341 | 3/1998 |
| JP | 3194657 | 7/2001 |
| WO | 2004 053019 | 6/2004 |
| WO | 2007 102683 | 9/2007 |
| WO | 2008 020611 | 2/2008 |

OTHER PUBLICATIONS

U.S. Appl. No. 13/509,434, filed May 11, 2012, Yokoyama, et al.
Hosokawa, C. et al., Japan Society of Applied Physics Ninth Workshop Preprint, pp. 55-61, (2001).
Wakimoto, T. "Optimization of Driving Lifetime Durability in Organic LED Devices Using Phosphorescent Guest Emitter", Japan Society of Applied Physics Ninth Workshop Preprint, pp. 23-31, (2001).
"Organic LEDs Using Hexaphenyl benzene Derivatives", Fiftieth Meeting of Japan Society of Applied Physics and Related Societies, 28p-A-6, Lecture Preprint, p. 1413, (2003).
Japan Society of Applied Physics, Journal of Organic Molecules/Bioelectronics Section, vol. 11, No. 1, pp. 13-19, (2000).
International Search Report issued Dec. 1, 2009 in PCT/JP09/066450 filed Sep. 18, 2009.

\* cited by examiner

*Primary Examiner* — Gregory Clack
(74) *Attorney, Agent, or Firm* — Oblon, Spivak, McClelland, Maier & Neustadt, L.L.P.

(57) ABSTRACT

The present invention provides an organic compound having excellent properties, which is excellent in electron-injection/transport performance, has hole-blocking ability and is high stability in a thin-film state, as a material for an organic electroluminescence device having a high efficiency and a high durability, and provides is an organic electroluminescence device having a high efficiency and a high durability using the compound. The present invention relates to a compound having a substituted anthracene ring structure and a pyridoindole ring structure represented by general formula (1); and an organic electroluminescence device having a pair of electrodes and at least one organic layer interposed between the electrodes in which the at least one organic layer contains the compound.

[Chem. 1]

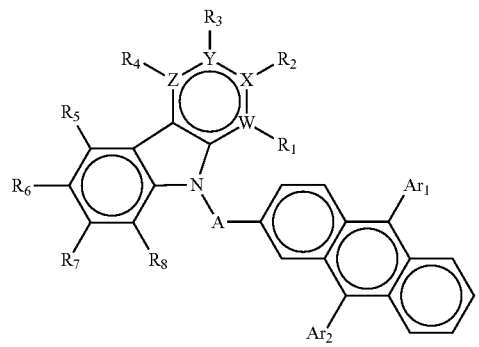

(1)

8 Claims, 7 Drawing Sheets

COMPOUND HAVING SUBSTITUTED ANTHRACENE RING STRUCTURE AND PYRIDOINDOLE RING STRUCTURE AND ORGANIC ELECTROLUMINESCENCE DEVICE

TECHNICAL FIELD

The present invention relates to a compound suitable for an organic electroluminescence device which is a self-luminescent device suitable for various displaying devices and a device. More specifically, it relates to a compound having a substituted anthracene ring structure and a pyridoindole ring structure and to an organic electroluminescence device using the compound.

BACKGROUND ART

Since organic electroluminescence devices are self-luminescent devices, they are bright and excellent in visibility as compared with liquid-crystalline devices and capable of giving clear display, so that the organic electroluminescence devices have been actively studied.

In 1987, C. W. Tang et al. of Eastman Kodak Company put an organic electroluminescence device using organic materials into practical use by developing a device having a multi-layered structure wherein various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1000 cd/m2 or more at a voltage of 10 V or lower (see e.g., Patent Documents 1 and 2).
Patent Document 1: JP-A-8-48656
Patent Document 2: Japanese Patent No. 3194657

To date, many improvements have been performed for practical utilization of the organic electroluminescence devices, and high efficiency and durability have been achieved by an electroluminescence device wherein an anode, a hole-injection layer, a hole-transport layer, a light-emitting layer, an electron-transport layer, an electron-injection layer, and a cathode are sequentially provided on a substrate, to further segmentalize various roles (see e.g., Non-Patent Document 1).
Non-Patent Document 1: Japan Society of Applied Physics Ninth Workshop Preprint, pp. 55-61 (2001)

Moreover, for the purpose of further improvement of luminous efficiency, utilization of triplet exciton has been attempted and utilization of a phosphorescent material has been investigated (see e.g., Non-Patent Document 2).
Non-Patent Document 2: Japan Society of Applied Physics Ninth Workshop Preprint, pp. 23-31 (2001)

The light-emitting layer can be also prepared by doping a charge-transport compound, generally called a host material, with a fluorescent material or a phosphorescent material. As described in the above-mentioned Workshop Preprints, the choice of the organic materials in organic electroluminescence devices remarkably affects various properties such as efficiency and durability of the devices.

In the organic electroluminescence devices, the charges injected from the both electrode are recombined in the light-emitting layer to attain light emission. However, since the mobility of holes is higher than the mobility of electrons, a problem of reduction in efficiency caused by a part of the holes passing through the light-emitting layer arises. Therefore, it is required to develop an electron-transport material in which the mobility of electrons is high.

A representative light-emitting material, tris(8-hydroxyquinoline)aluminum (hereinafter referred to as Alq3) is commonly used also as an electron-transport material. However, since it has a work function of 5.8 eV, it cannot be considered that the material has hole-blocking capability.

As a technique to prevent the passing of a part of holes through the light-emitting layer and to improve probability of charge recombination in the light-emitting layer, there is a method of inserting a hole-blocking layer. As hole-blocking materials, there have been hitherto proposed triazole derivatives (see e.g., Patent Document 3), bathocuproine (hereinafter referred to as BCP), a mixed ligand complex of aluminum (BAlq) (see e.g., Non-Patent Document 2), and the like.

On the other hand, as an electron-transport material excellent in hole-blocking ability, there is proposed 3-(4-biphenylyl)-4-phenyl-5-(4-t-butylphenyl)-1,2,4-triazole (hereinafter referred to as TAZ) (see e.g., Patent Document 3).
Patent Document 3: Japanese Patent No. 2734341

Since TAZ has a work function as large as 6.6 eV and thus exhibits a high hole-blocking ability, it is used as an electron-transport hole-blocking layer to be laminated onto the cathode side of a fluorescence-emitting layer or phosphorescence-emitting layer prepared by vacuum deposition, coating or the like, and contributes to increase the efficiency of organic electroluminescence devices (see e.g., Non-Patent Document 3).
Non-Patent Document 3: Fiftieth Meeting of Japan Society of Applied Physics and Related Societies, 28p-A-6 Lecture Preprint, p. 1413 (2003)

However, TAZ has a great problem of having low electron transport property, and it is necessary to prepare an organic electroluminescence device in combination with an electron-transport material having a higher electron transport property (see e.g., Non-Patent Document 4).
Non-Patent Document 4: Japan Society of Applied Physics, Journal of Organic Molecules/Bioelectronics Section, Vol. 11, No. 1, pp. 13-19 (2000)

Further, BCP has a work function as large as 6.7 eV and a high hole-blocking ability, but has a low glass transition point (Tg) which is 83° C., so that it is poor in thin-film stability and thus it cannot be considered that it sufficiently functions as a hole-blocking layer.

All the materials are insufficient in thin-film stability or are insufficient in the function of blocking holes. In order to improve characteristic properties of the organic electroluminescence devices, it is desired to develop an organic compound which is excellent in electron-injection/transport performances and hole-blocking ability and is highly stable in a thin-film state.

SUMMARY OF THE INVENTION

Problems to be Solved by the Invention

Objects of the present invention are to provide an organic compound having excellent properties, which is excellent in electron-injection/transport performances, has hole-blocking ability and has high stability in a thin-film state, as a material for an organic electroluminescence device having a high efficiency and a high durability, and to provide an organic electroluminescence device having a high efficiency and a high durability using the compound.

As physical properties of the organic compound to be provided by the invention, there may be mentioned (1) a good electron injection characteristic, (2) a high electron mobility, (3) an excellent hole-blocking ability, (4) good stability in a thin-film state, and (5) excellent thermal resistance. In addition, as physical properties of the organic electroluminescence device to be provided by the invention, there may be mentioned (1) high luminous efficiency, (2) low emission initiation voltage, (3) low practical driving voltage.

Means for Solving the Problems

Thus, in order to achieve the above objects, the present inventors have designed and chemically synthesized compounds having a substituted anthracene ring structure and a pyridoindole ring structure, with focusing on the fact that the pyridoindole ring structure has an excellent electron-transport performance and is excellent in thermal resistance. The present inventors have experimentally produced various organic electroluminescence devices using the compounds, and have extensively performed property evaluation of the devices. As a result, they have accomplished the invention.

That is, the invention provides: a compound having a substituted anthracene ring structure and a pyridoindole ring structure, represented by the following general formula (1); and an organic electroluminescence device comprising a pair of electrodes and at least one organic layer interposed between the electrodes, wherein the at least one organic layer contains the compound:

[Chem. 1]

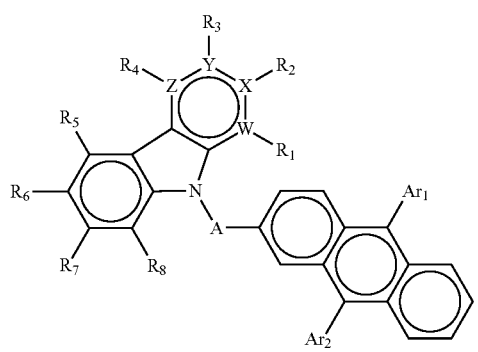

(1)

(wherein $Ar_1$ and $Ar_2$ may be the same or different from each other and each represents a substituted or unsubstituted aromatic hydrocarbon group, $R_1$ to $R_8$ may be the same or different and each represents a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, a substituted or unsubstituted aromatic heterocyclic group, or a substituted or unsubstituted condensed polycyclic aromatic group, W, X, Y and Z each represents a carbon atom or a nitrogen atom, and A represents a single bond or a divalent group represented by the following general formula (A1), provided that only one of W, X, Y and Z is a nitrogen atom and the nitrogen atom does not have a substituent $R_1$ to $R_4$):

[Chem. 2]

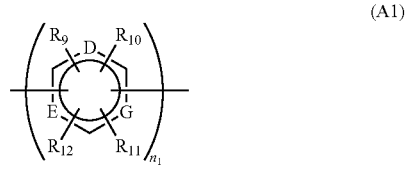

(A1)

(wherein n1 represents an integer of 1 or 2, $R_9$ to $R_{12}$ may be the same or different and each represents a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, or a substituted or unsubstituted aromatic heterocyclic group, D, E and G each represents a carbon atom or a nitrogen atom, provided that when all of or one or two of D, E and G are a nitrogen atom, the nitrogen atom does not have a substituent $R_9$ to $R_{12}$ or bonding group and when n1 is an integer of 2, a plurality of $R_9$'s, $R_{10}$'s, $R_{11}$'s, $R_{12}$'s, D's, E's or G's may be different from each other).

The "aromatic hydrocarbon group" in the substituted or unsubstituted aromatic hydrocarbon group represented by $Ar_1$ or $Ar_2$ in general formula (1) specifically includes a phenyl group, a biphenylyl group, a terphenylyl group, a naphthyl group, an anthryl group and a phenanthryl group.

The "substituent" in the substituted aromatic hydrocarbon group represented by $Ar_1$ or $Ar_2$ in general formula (1) specifically includes a fluorine atom, a chlorine atom, a cyano group, a hydroxyl group, a nitro group, a linear or branched alkyl group having 1 to 6 carbon atoms, a cyclopentyl group, a cyclohexyl group, a linear or branched alkoxy group having 1 to 6 carbon atoms, a dialkylamino group substituted with a linear or branched alkyl group having 1 to 6 carbon atoms, phenyl group, naphthyl group, anthryl group, styryl group, pyridyl group, pyridoindolyl group, quinolyl group and benzothiazolyl group. These substituents may be further substituted.

The "aromatic hydrocarbon group", the "aromatic heterocyclic group" and the "condensed polycyclic aromatic group" in the substituted or unsubstituted aromatic hydrocarbon group, the substituted or unsubstituted aromatic heterocyclic group, or the substituted or unsubstituted condensed polycyclic aromatic group, represented by $R_1$ to $R_8$ in general formula (1), specifically include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a triazyl group, a pyrimidyl group, a furanyl group, a pyrazyl group, a thienyl group, a quinolyl group, an isoquinolyl group, a benzofuranyl group, a benzothiophenyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothiophenyl group, a naphthyridinyl group, a phenanthrolinyl group and an acridinyl group.

The "substituent" in the substituted aromatic hydrocarbon group, the substituted aromatic heterocyclic group, or the substituted condensed polycyclic aromatic group, represented by $R_1$ to $R_8$ in general formula (1), specifically includes a fluorine atom, a chlorine atom, a trifluoromethyl group, a linear or branched alkyl group having 1 to 6 carbon atoms, a phenyl group, a biphenylyl group, a terphenylyl group, a tetrakisphenyl group, a styryl group, a naphthyl group, a fluorenyl group, a phenanthryl group, an indenyl group and a pyrenyl group, and these substituents may be further substituted.

The linear or branched alkyl group having 1 to 6 carbon atoms, represented by $R_1$ to $R_8$ in general formula (1), specifically includes a methyl group, an ethyl group, an n-propyl group, an i-propyl group, an n-butyl group, an i-butyl group, a t-butyl group, an n-pentyl group, an i-pentyl group, a t-pentyl group, an n-hexyl group, an i-hexyl group and a t-hexyl group.

The divalent group represented by A in general formula (1) includes a phenylene group, a biphenylene group, a pyridylene group, a bipyridylene group, a pyrimidylene group, a bis-pyrimidylene group, a triazylene group, a bis-triazylene group, and a divalent group represented by the following general formula (A2):

[Chem.3]

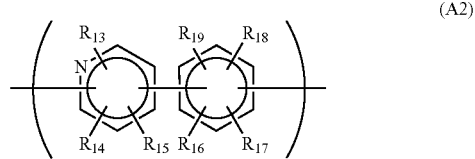

(A2)

(wherein $R_{13}$ to $R_{19}$ may be the same or different and each represents a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, or a substituted or unsubstituted aromatic heterocyclic group).

The "aromatic hydrocarbon group" and the "aromatic heterocyclic group" in the substituted or unsubstituted aromatic hydrocarbon group or the substituted or unsubstituted aromatic heterocyclic group, represented by $R_9$ to $R_{19}$ in general formula (A1) and general formula (A2), and the "substituent" thereof include the same groups as described in $R_1$ to $R_8$ of general formula (1).

Also, the linear or branched alkyl group having 1 to 6 carbon atoms, represented by $R_9$ to $R_{19}$ in general formula (A1) and general formula (A2), includes the same groups as described in $R_1$ to $R_8$ of general formula (1).

The compound having a substituted anthracene ring structure and a pyridoindole ring structure, which is represented by general formula (1) of the invention, is a novel compound, provides high electron mobility as compared with conventional electron-transport materials, has an excellent hole-blocking ability, and is stable in a thin-film state.

The compound having a substituted anthracene ring structure and a pyridoindole ring structure, which is represented by general formula (1) of the invention, can be used as a constituent material for an electron-transport layer of an organic electroluminescence device (hereinafter, abbreviated as organic EL device). The use of the material exhibiting a higher electron injection/mobility as compared with conventional materials provides effects of improving electron transport efficiency from the electron-transport layer to a light-emitting layer to enhance luminous efficiency and also lowering a driving voltage to enhance durability of the organic EL device.

The compound having a substituted anthracene ring structure and a pyridoindole ring structure, which is represented by general formula (1) of the invention, can be also used as a constituent material for a hole-blocking layer of an organic EL device. The use of the material excellent in hole-blocking ability and also excellent in electron transport property as compared with conventional materials and having high stability in a thin-film state provides effects of lowering a driving voltage, improving current resistance, and enhancing maximum emission luminance of the organic EL device, while exhibiting a high luminous efficiency.

The compound having a substituted anthracene ring structure and a pyridoindole ring structure, which is represented by general formula (1) of the invention, can be also used as a constituent material for a light-emitting layer of an organic EL device. The use of a light-emitting layer prepared by using the material of the invention excellent in electron transport property as compared with conventional materials and having a wide band-gap as a host material for the light-emitting layer and making a fluorescent material or a phosphorescent material, called a dopant, carried thereon provides an effect of realizing an organic EL device exhibiting a lowered driving voltage and having an improved luminous efficiency.

The organic EL device of the invention uses the compound having a substituted anthracene ring structure and a pyridoindole ring structure, which compound exhibits high electron mobility as compared with conventional electron-transport materials, has an excellent hole-blocking ability and is stable in a thin-film state. Therefore, it becomes possible to realize high efficiency and high durability.

Advantageous Effects of the Invention

The compound having a substituted anthracene ring structure and a pyridoindole ring structure of the invention is useful as a constituent material for an electron-transport layer, a hole-blocking layer, or a light-emitting layer of an organic EL device, and the compound exhibits an excellent hole-blocking ability, is stable in a thin-film state, and has excellent thermal resistance. The organic EL device of the invention exhibits a high luminous efficiency, whereby the practical driving voltage of the device can be lowered. By lowering the light emission initiation voltage, the durability can be improved.

MODE FOR CARRYING OUT THE INVENTION

Figure 1:
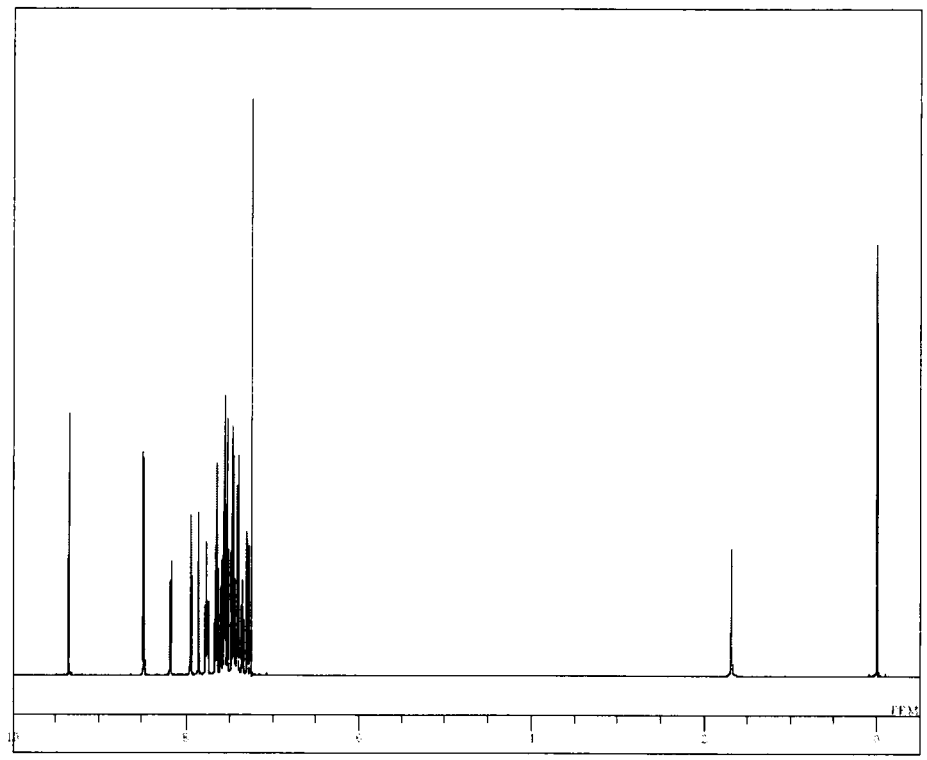
FIG. 1 is a 1H-NMR chart of the compound (Compound 3) of Invention Example 1.

The compound having a substituted anthracene ring structure and a pyridoindole ring structure is a novel compound, and this compound can be synthesized, for example, as follows. A corresponding halogenoanilinopyridine is subjected to a cyclization reaction with a palladium catalyst to synthesize a pyridoindole ring (see, for example, Non-Patent Document 5) and then condensed with a halide of various aromatic hydrocarbon compounds, condensed polycyclic aromatic compounds or aromatic heterocyclic compounds, whereby a compound having a corresponding pyridoindole ring structure can be synthesized. Furthermore, the compound having a corresponding pyridoindole ring structure is subjected to a cross-coupling reaction such as Suzuki coupling (see, for example, Non-Patent Document 6) with a boronic acid or boronic acid ester having an anthracene ring structure (see, for example, Patent Document 4) synthesized by a known method, whereby a compound having a substituted anthracene ring structure and a pyridoindole ring structure can be synthesized.

Non-Patent Document 5: J. Chem. Soc., Perkin Trans. 1, p. 1505 (1999)

Non-Patent Document 6: Synthesis, 1 (1976)

Patent Document 4: International Publication WO 2005/097756

Among the compounds having a substituted anthracene ring structure and a pyridoindole ring structure, which is represented by general formula (1), specific examples of preferred compounds are shown below, but the invention is not limited to these compounds.

[Chem. 4]

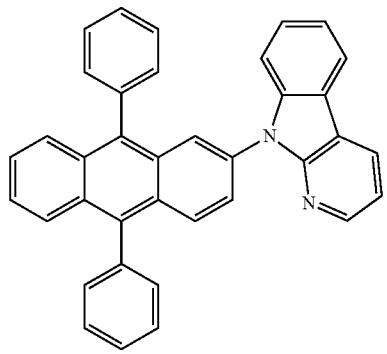

[Compound 2]

[Chem. 5]

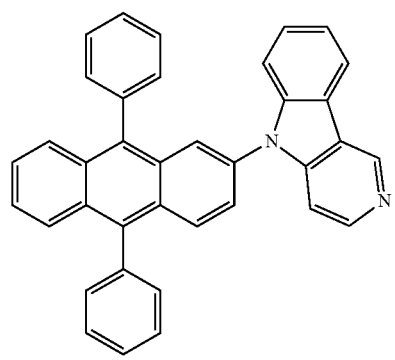

[Compound 3]

[Chem. 6]

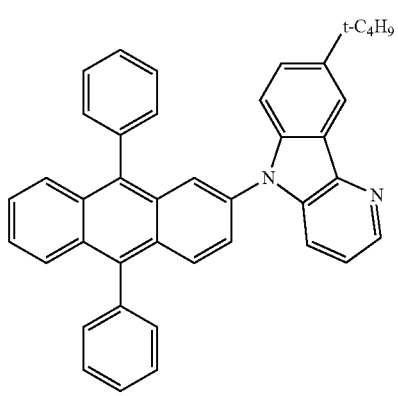

[Compound 4]

[Chem. 7]

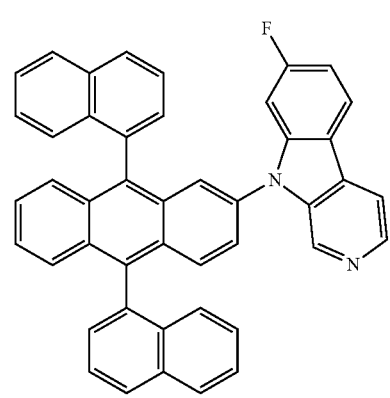

[Compound 5]

[Chem. 8]
[Compound 6]
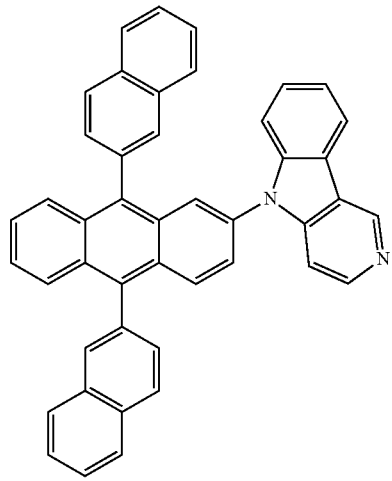
[Chem. 9]
[Compound 7]
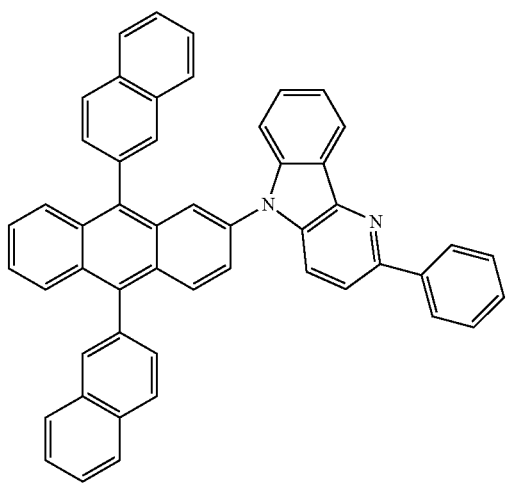
[Chem. 10]
[Compound 8]
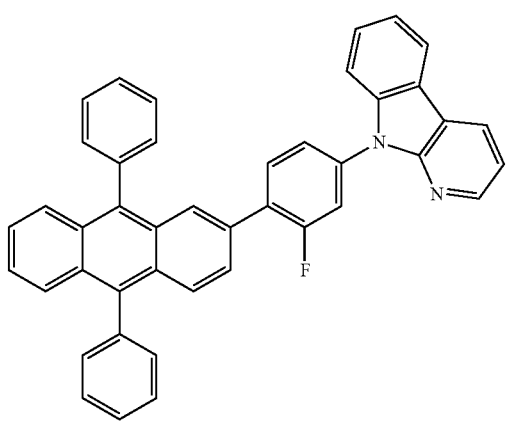
[Chem. 11]
[Compound 9]
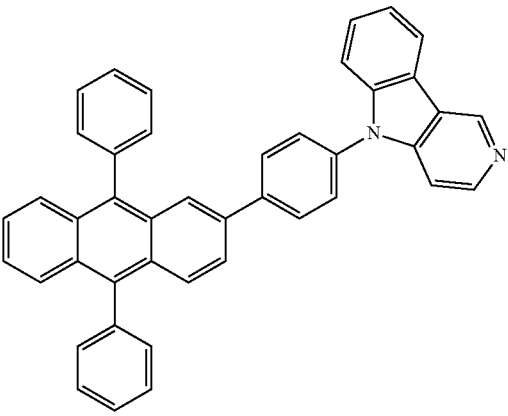
[Chem. 12]
[Compound 10]
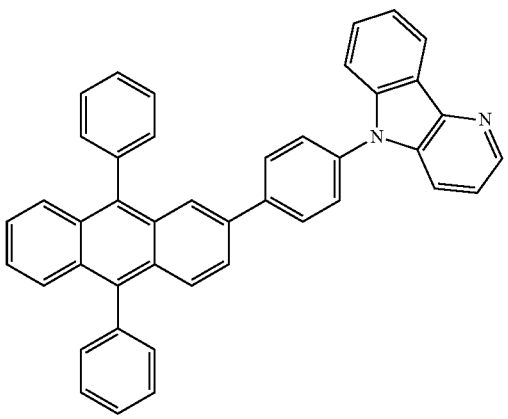
[Chem. 13]
[Compound 11]
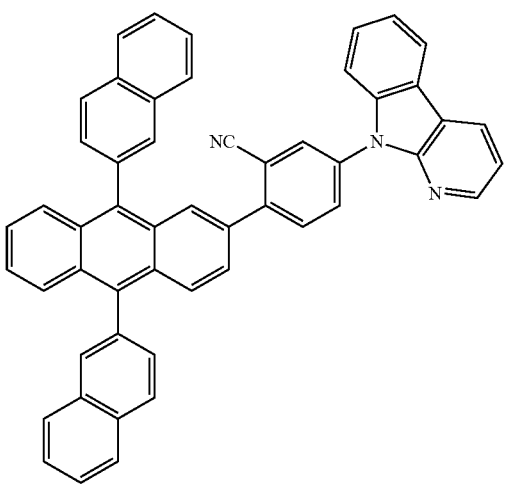

[Chem. 14]
[Compound 12]
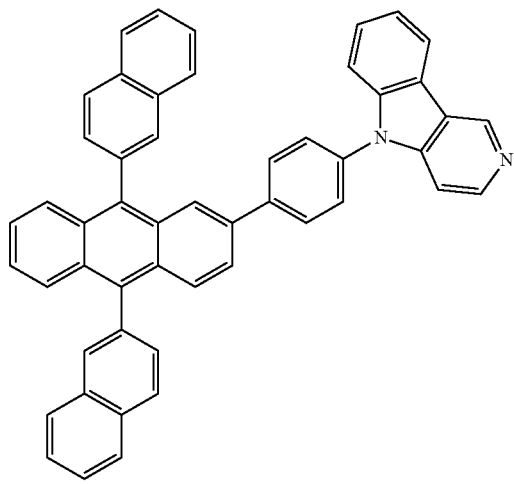
[Chem. 15]
[Compound 13]
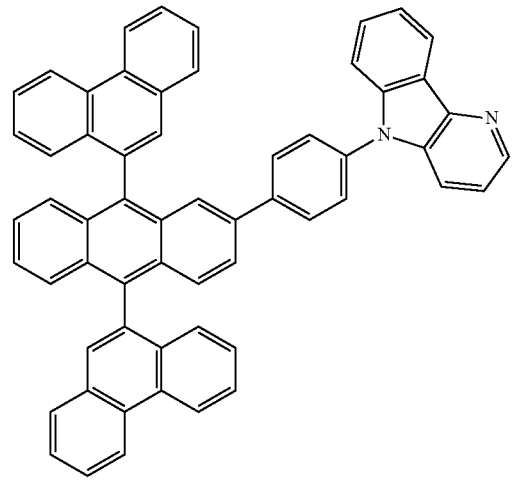
[Chem. 16]
[Compound 14]
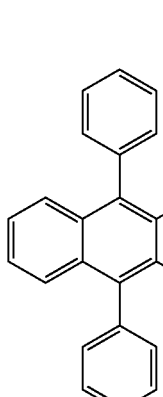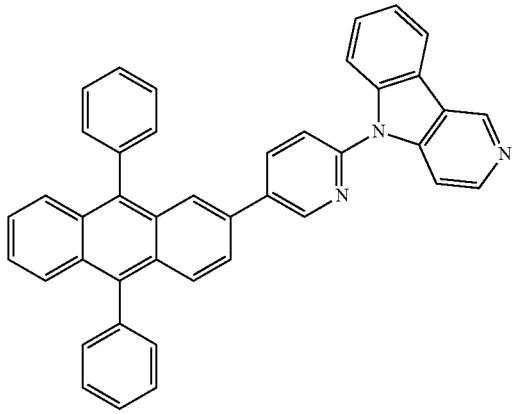
[Chem. 17]
[Compound 15]
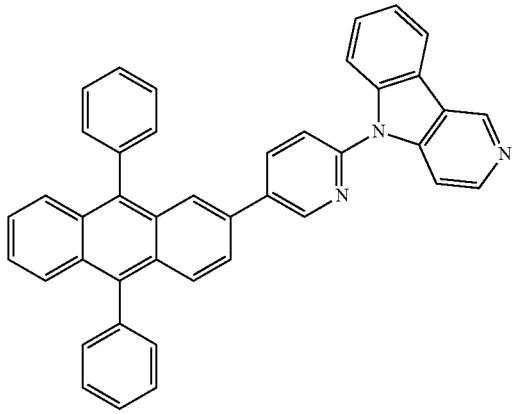
[Chem. 18]
[Compound 16]
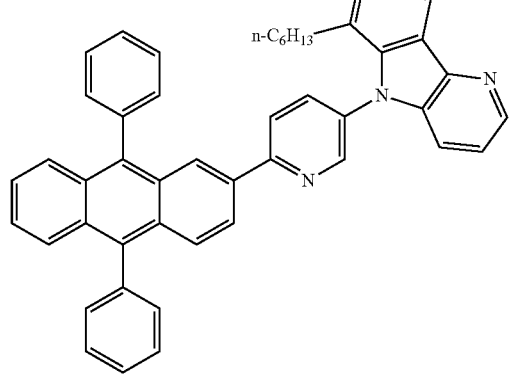
[Chem. 19]
[Compound 17]
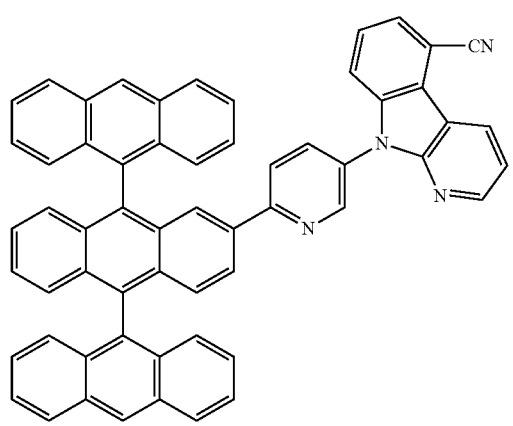

[Chem. 20]
[Compound 18]
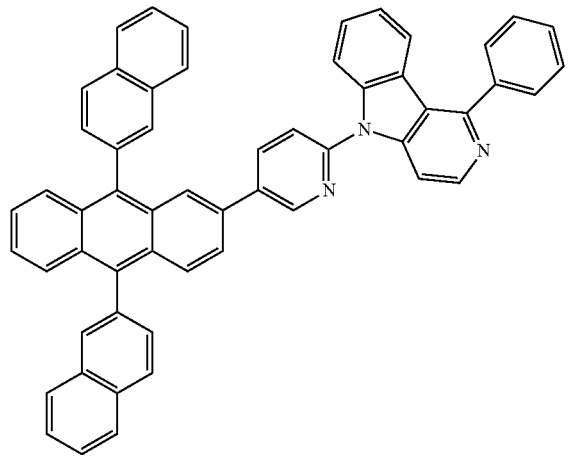
[Chem. 21]
[Compound 19]
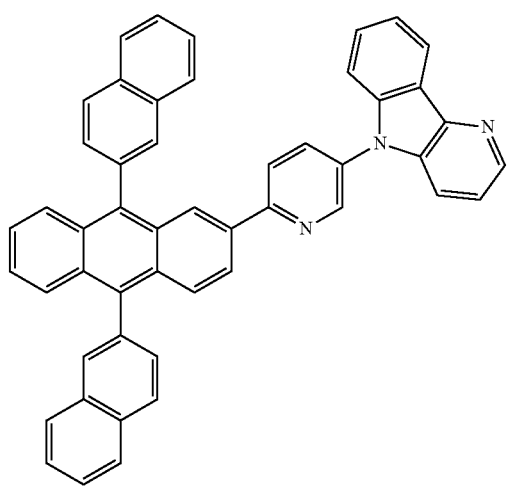
[Chem. 22]
[Compound 20]
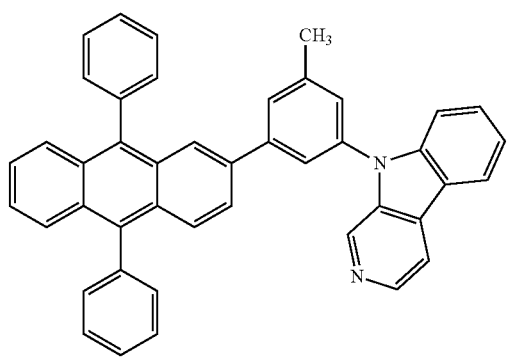
[Chem. 23]
[Compound 21]
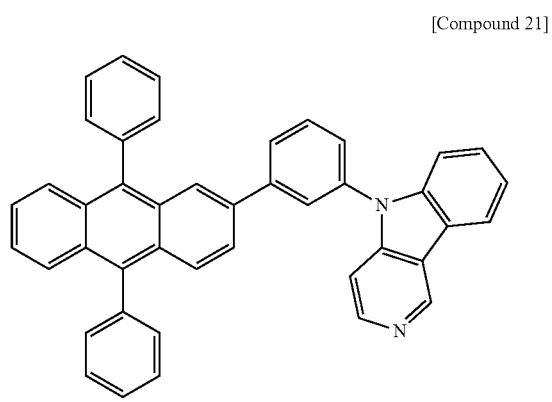
[Chem. 24]
[Compound 22]
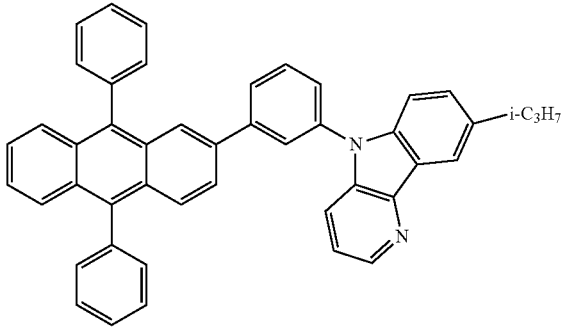
[Chem. 25]
[Compound 23]
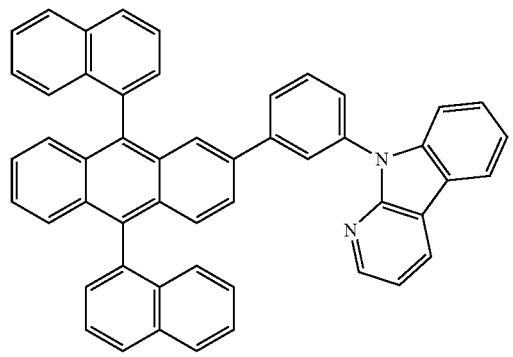

[Chem. 26]
[Compound 24]
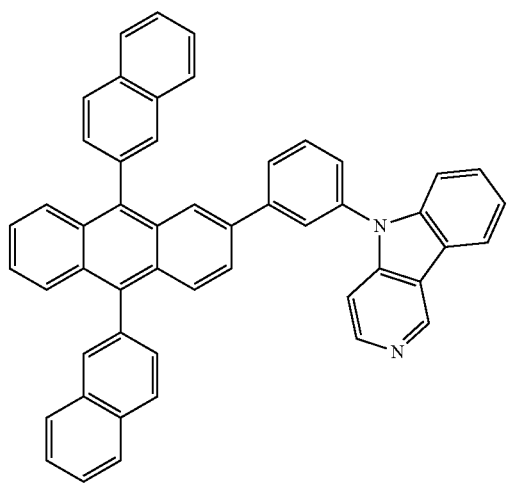
[Chem. 27]
[Compound 25]
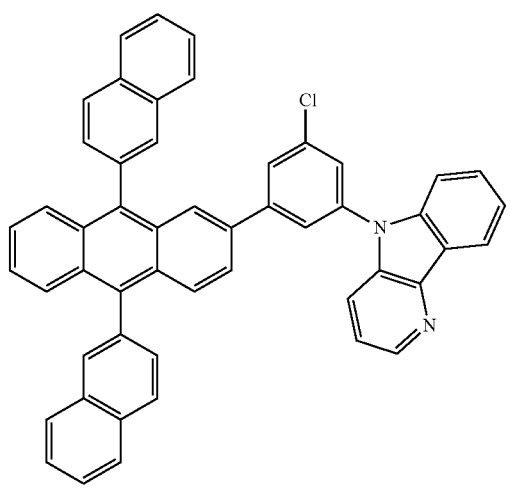
[Chem. 28]
[Compound 26]
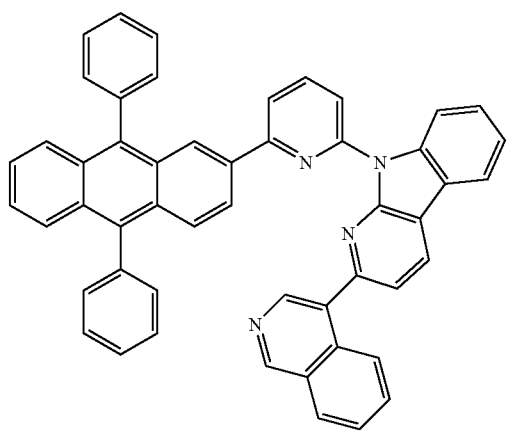
[Chem. 29]
[Compound 27]
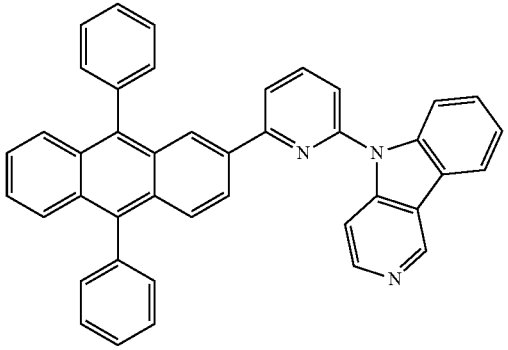
[Chem. 30]
[Compound 28]
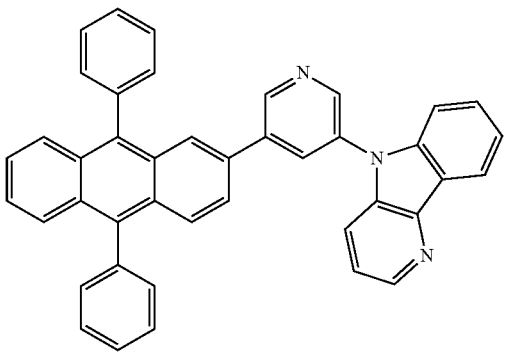
[Chem. 31]
[Compound 29]
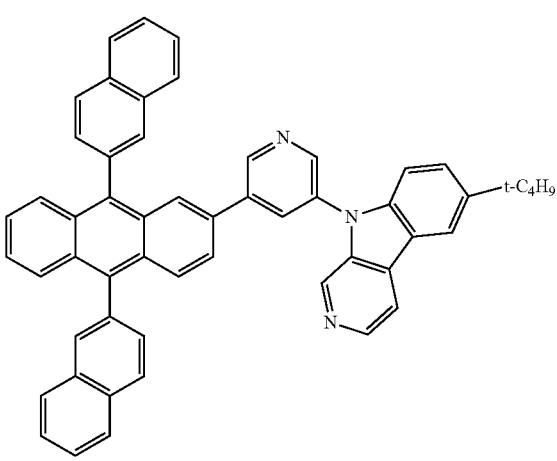

-continued
[Chem. 32]
[Compound 30]
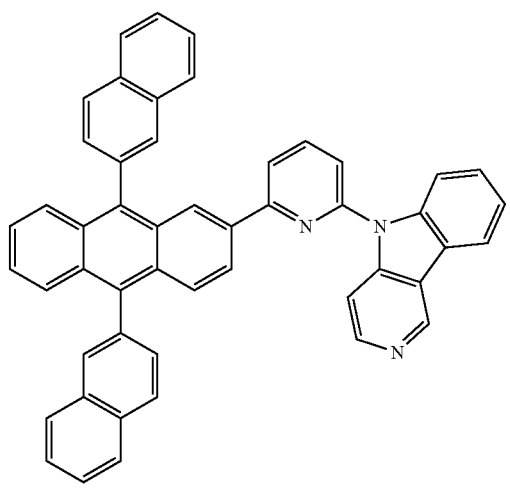
[Chem. 33]
[Compound 31]
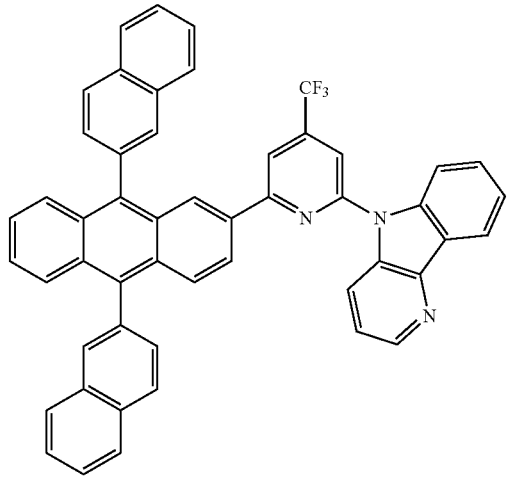
[Chem. 34]
[Compound 32]
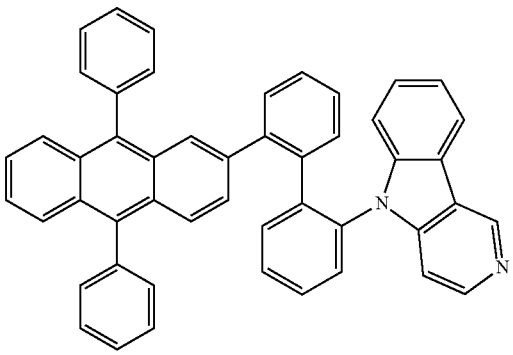
-continued
[Chem. 35]
[Compound 33]
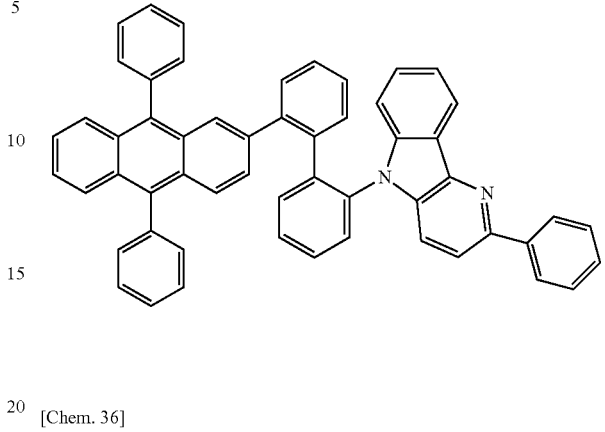
[Chem. 36]
[Compound 34]
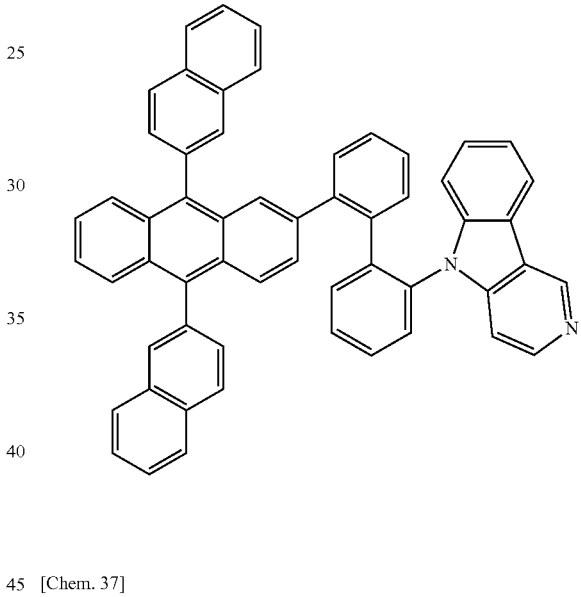
[Chem. 37]
[Compound 35]
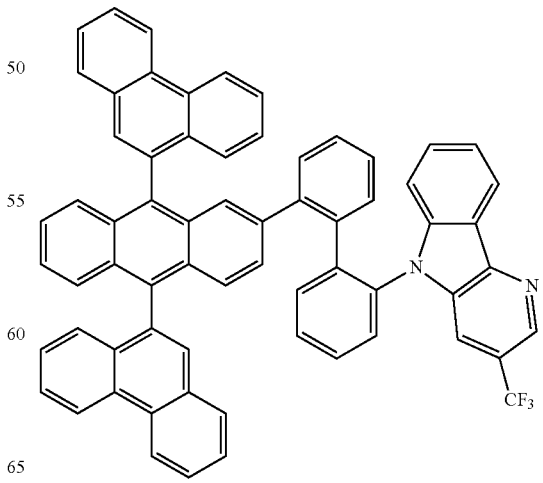

[Chem. 38]
[Compound 36]
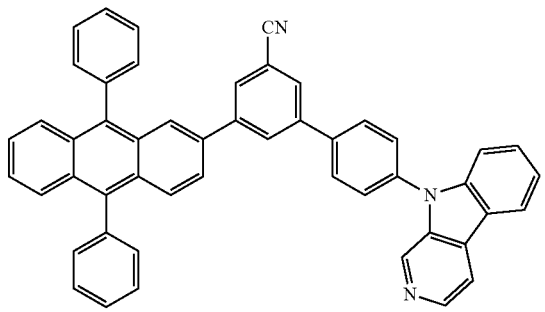
[Chem. 39]
[Compound 37]
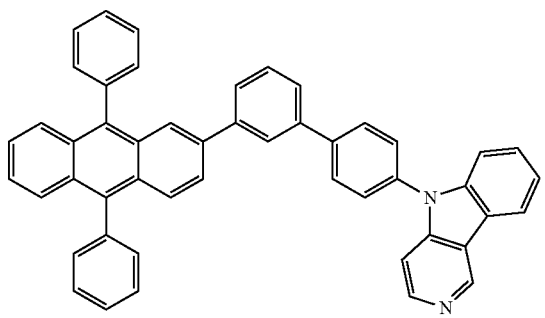
[Chem. 40]
[Compound 38]
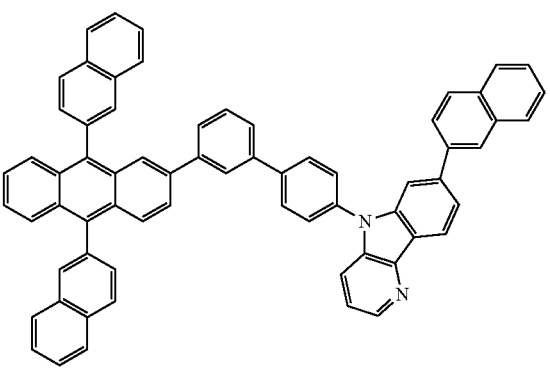
[Chem. 41]
[Compound 39]
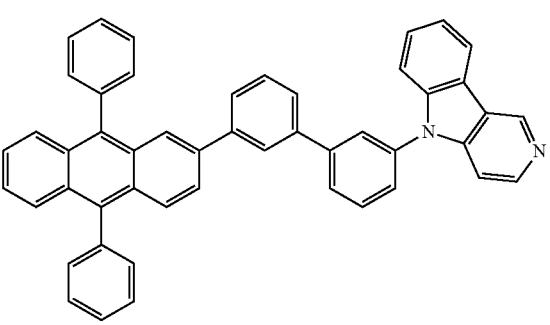
[Chem. 42]
[Compound 40]
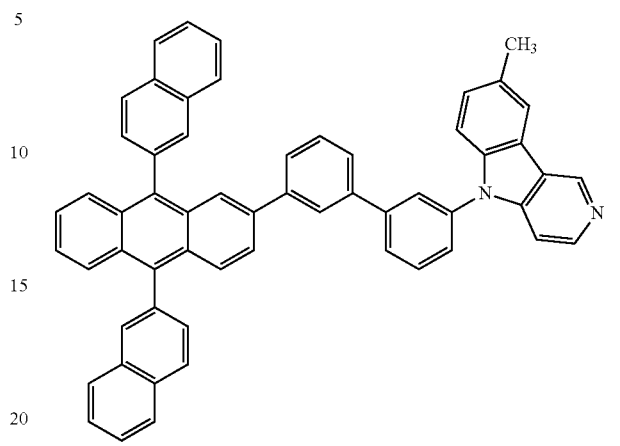
[Chem. 43]
[Compound 41]
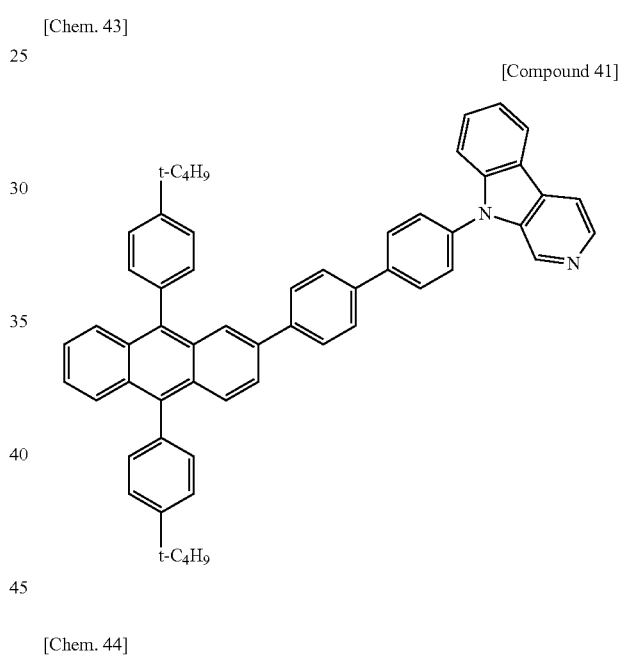
[Chem. 44]
[Compound 42]
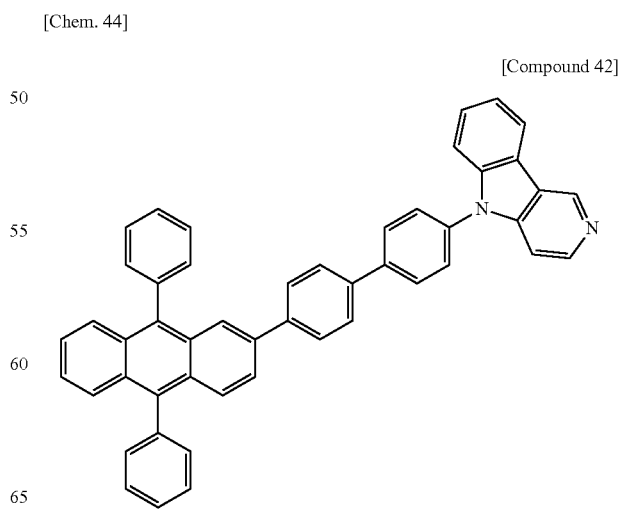

-continued
[Chem. 45]
[Compound 43]
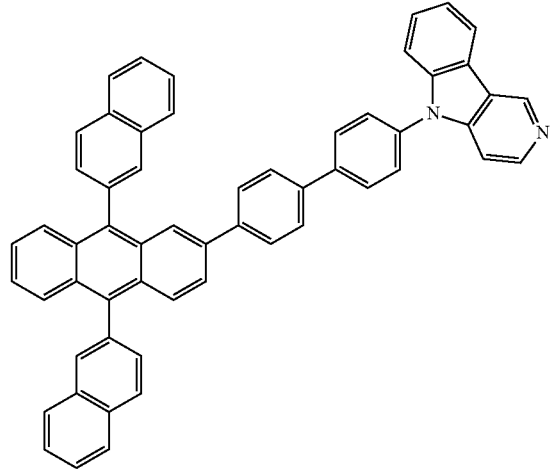
[Chem. 46]
[Compound 44]
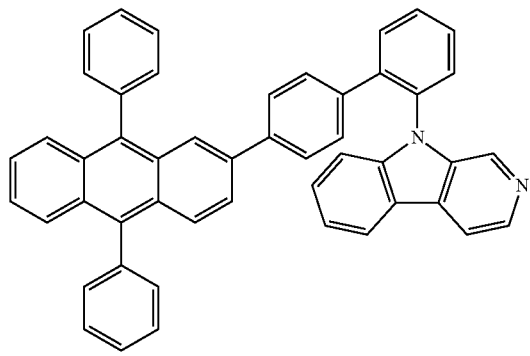
[Chem. 47]
[Compound 45]
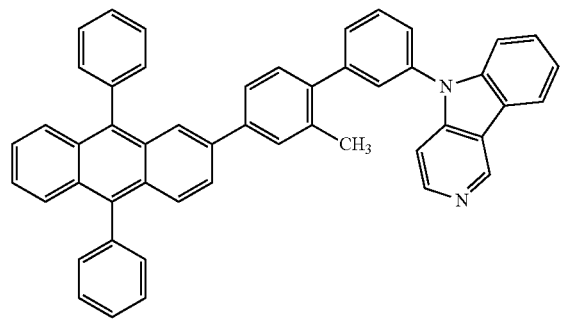
-continued
[Chem. 48]
[Compound 46]
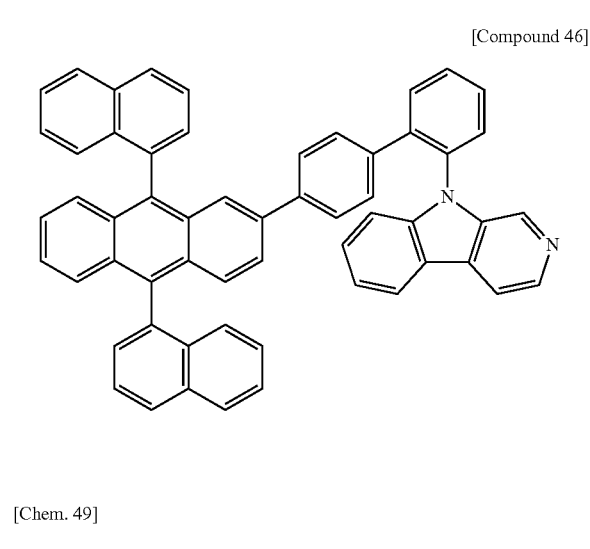
[Chem. 49]
[Compound 47]
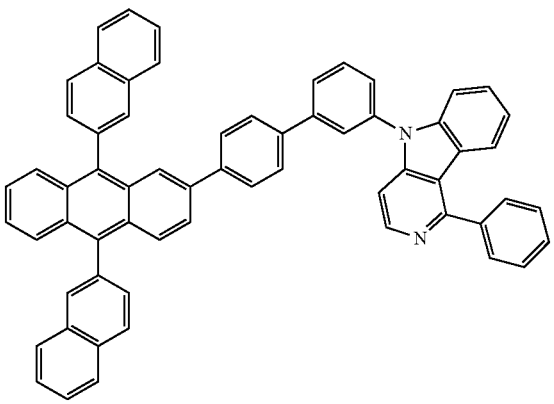
[Chem. 50]
[Compound 48]
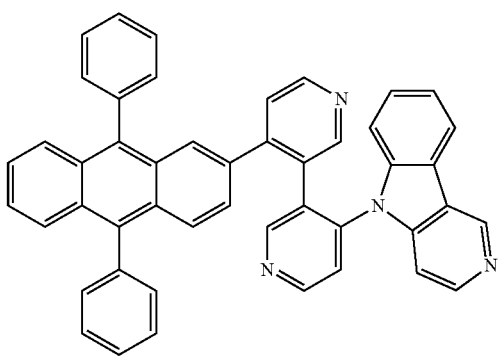

[Chem. 51]
[Compound 49]
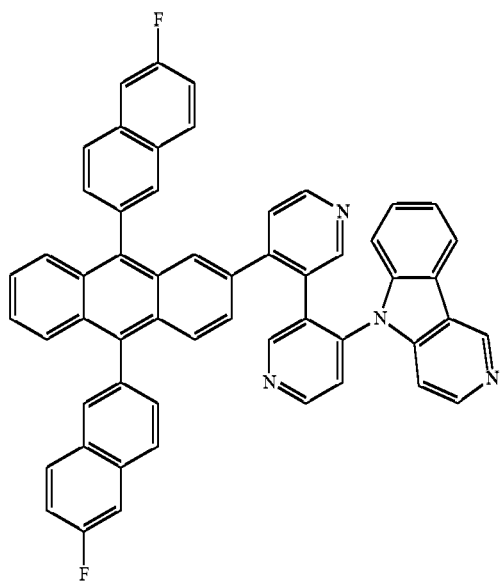
[Chem. 52]
[Compound 50]
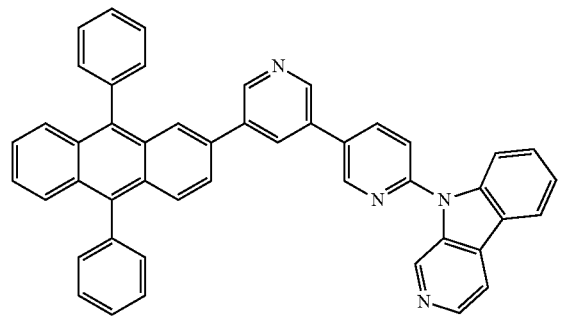
[Chem. 53]
[Compound 51]
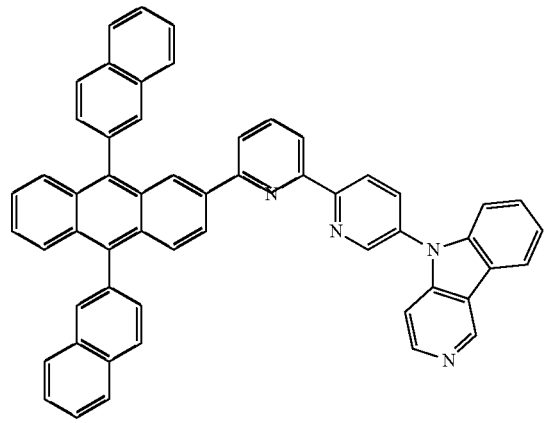
[Chem. 54]
[Compound 52]
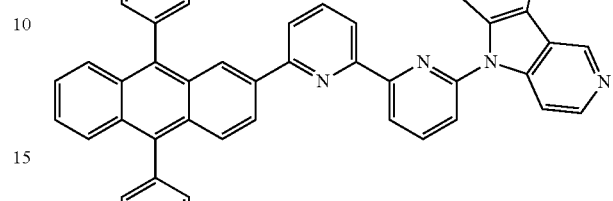
[Chem. 55]
[Compound 53]
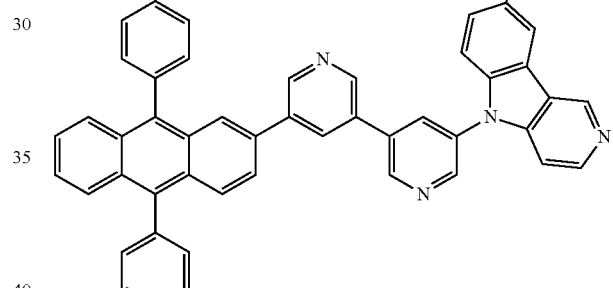
[Chem. 56]
[Compound 54]
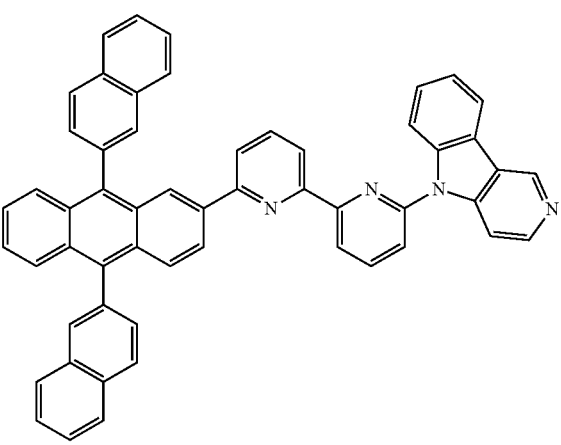

[Chem. 57]
[Compound 55]
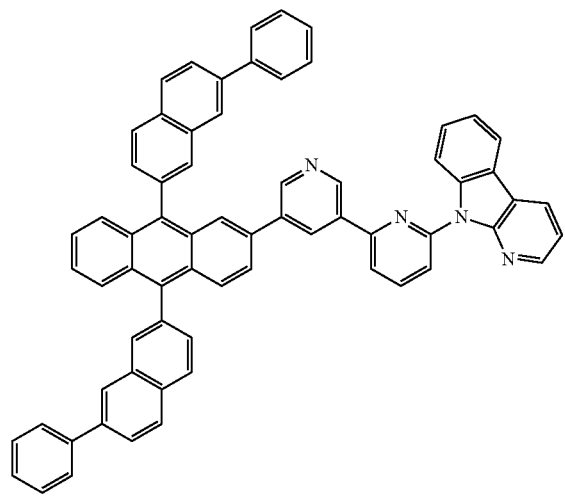
[Chem. 58]
[Compound 56]
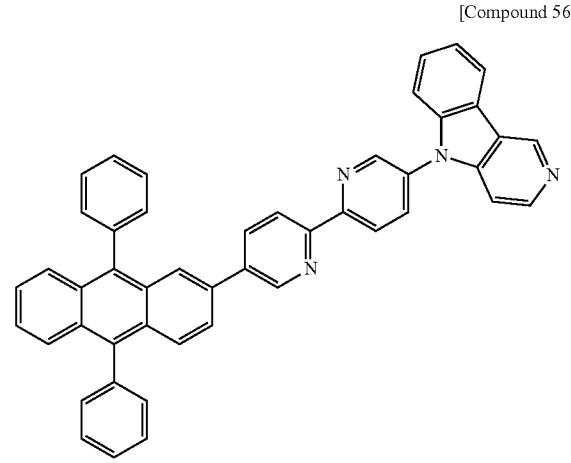
[Chem. 59]
[Compound 57]
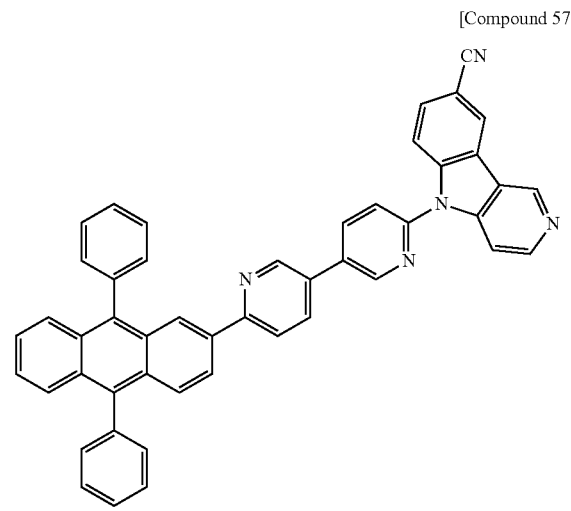
[Chem. 60]
[Compound 58]
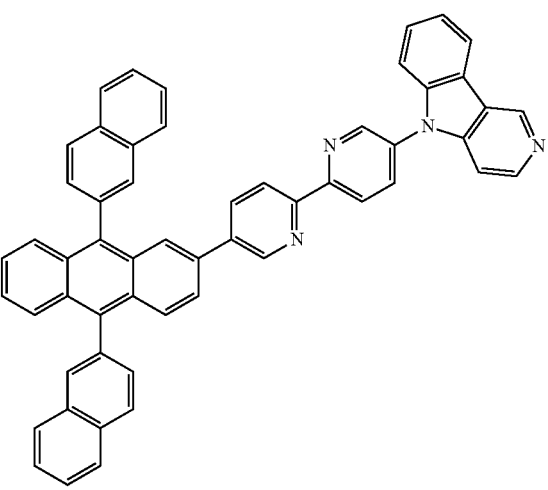
[Chem. 61]
[Compound 59]
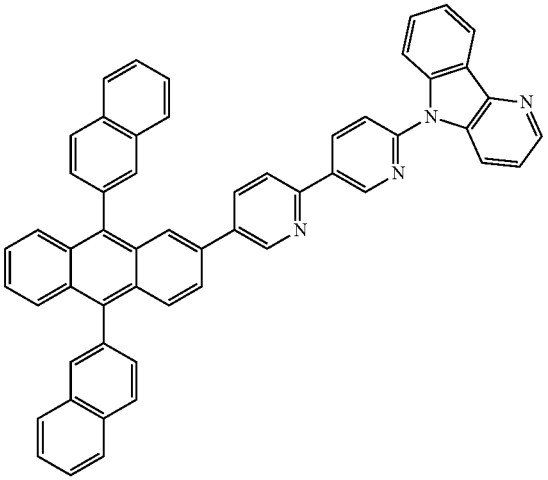

-continued
[Chem. 62]
[Compound 60]
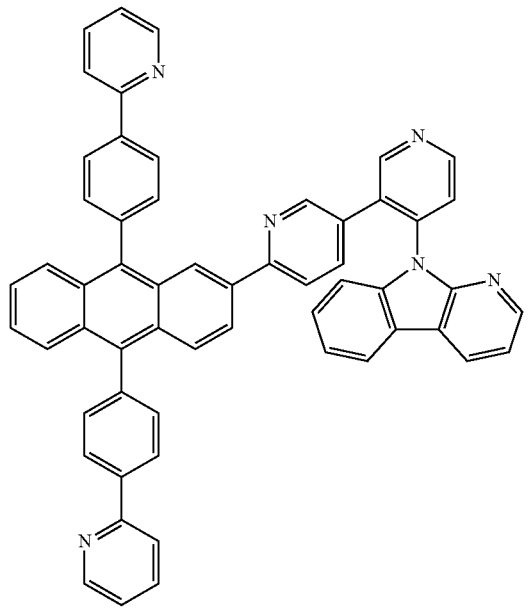
[Chem. 63]
[Compound 61]
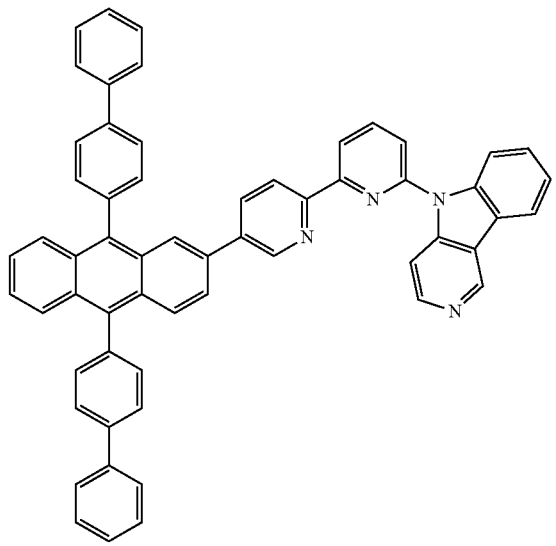
[Chem. 64]
[Compound 62]
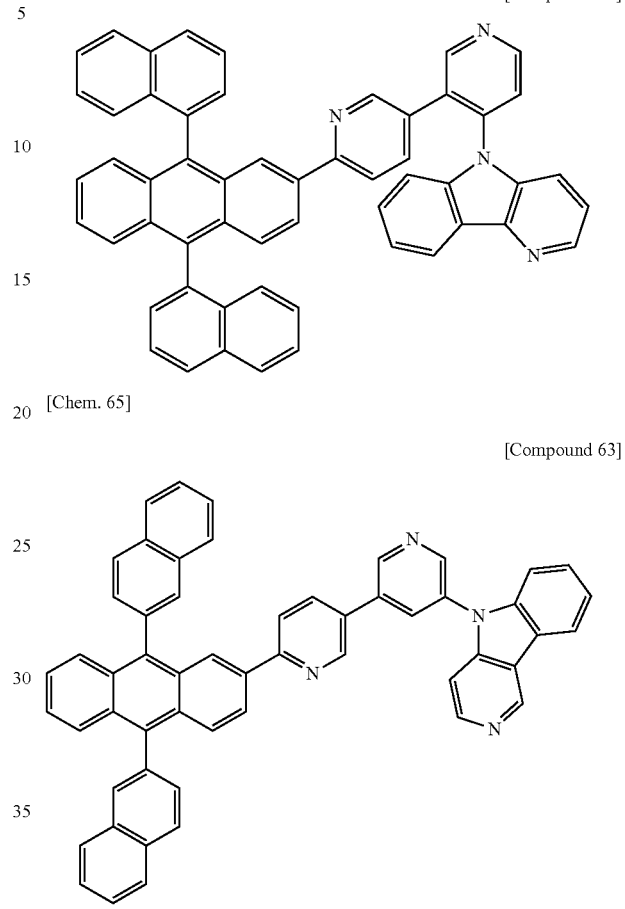
[Chem. 65]
[Compound 63]
[Chem. 66]
[Compound 64]
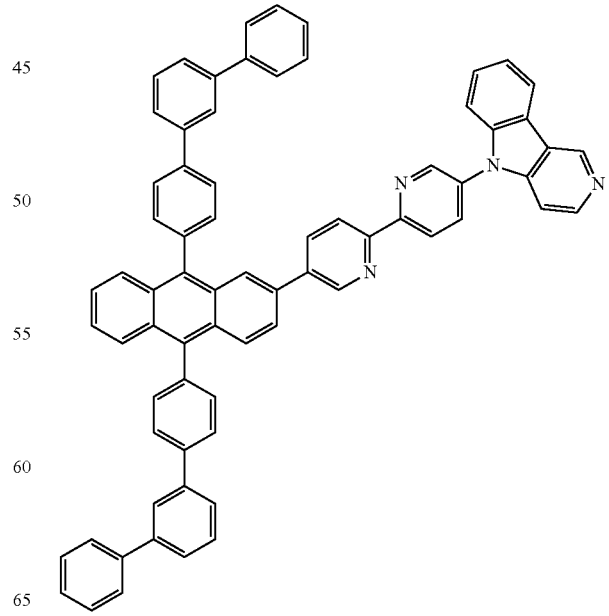

[Chem. 67]
[Compound 65]
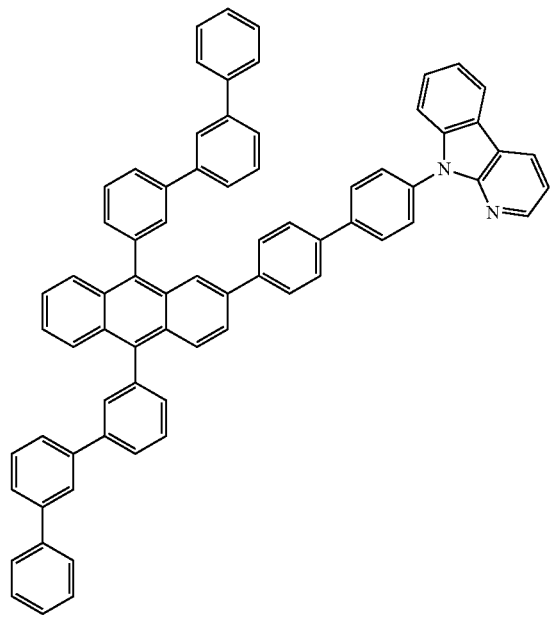
[Chem. 68]
[Compound 66]
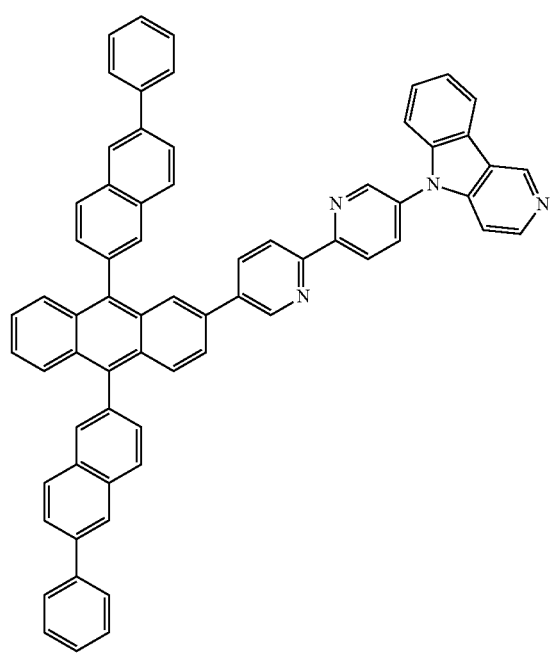
[Chem. 69]
[Compound 67]
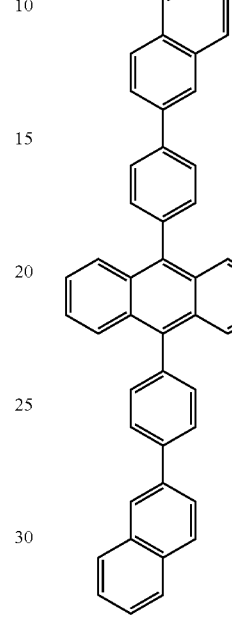
[Chem. 70]
[Compound 68]
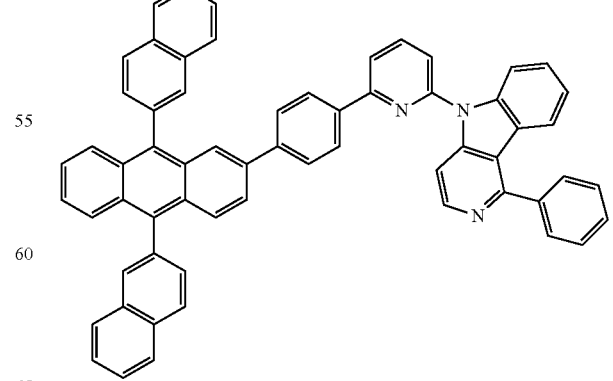

[Chem. 71]
[Compound 69]
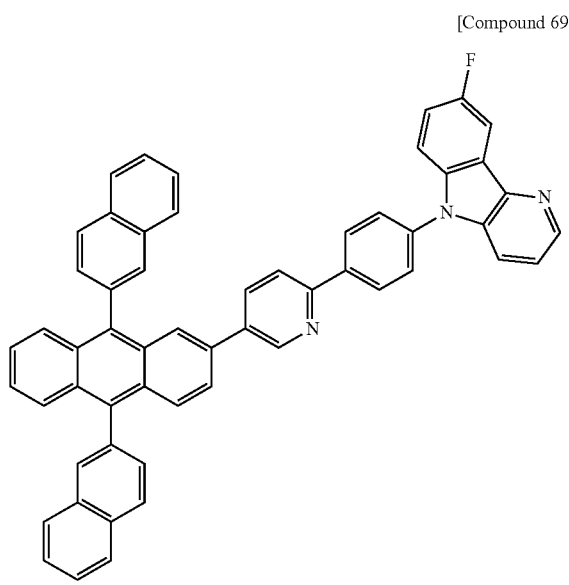
[Chem. 72]
[Compound 70]
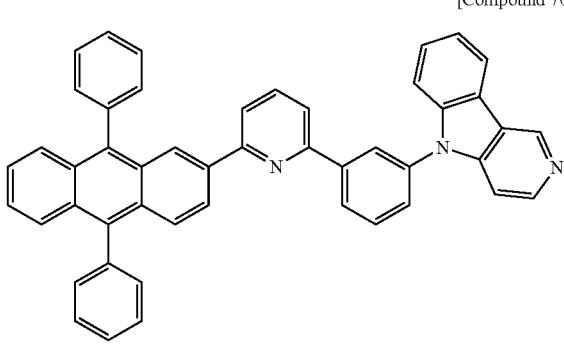
[Chem. 73]
[Compound 71]
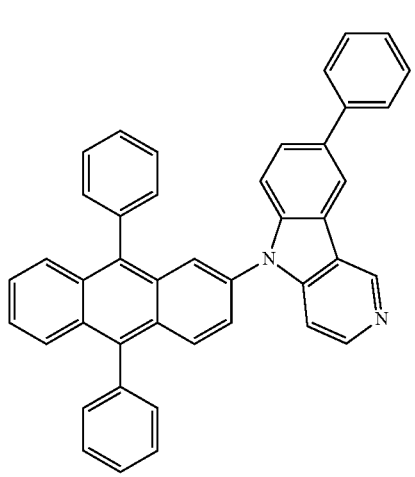
[Chem. 74]
[Compound 72]
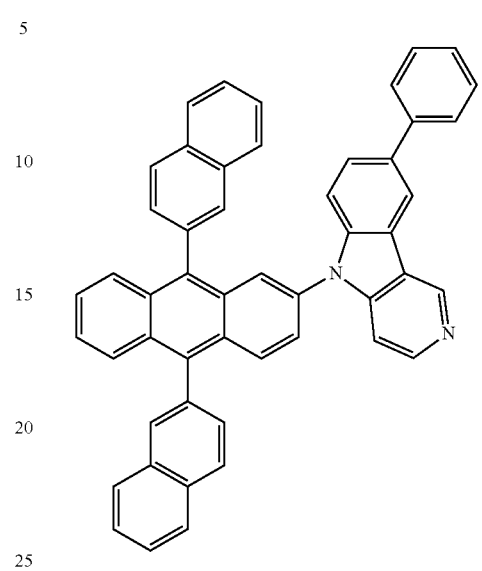
[Chem. 75]
[Compound 73]
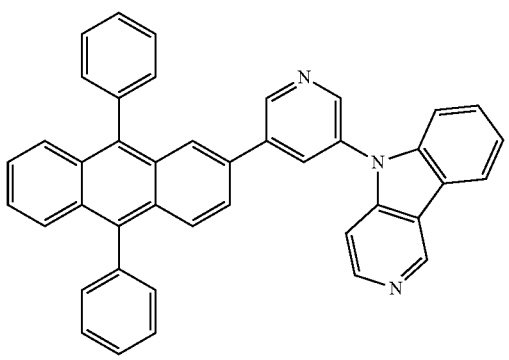
[Chem. 76]
[Compound 74]
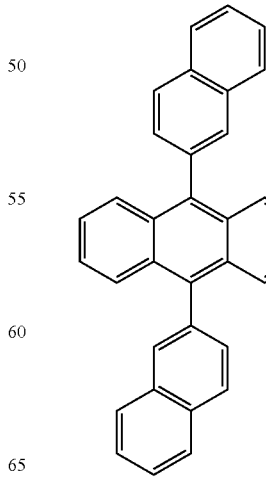

[Chem. 77]

[Compound 75]

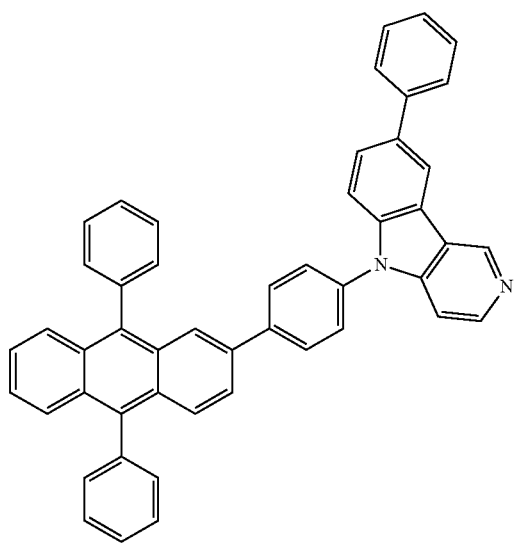

[Chem. 78]

[Compound 76]

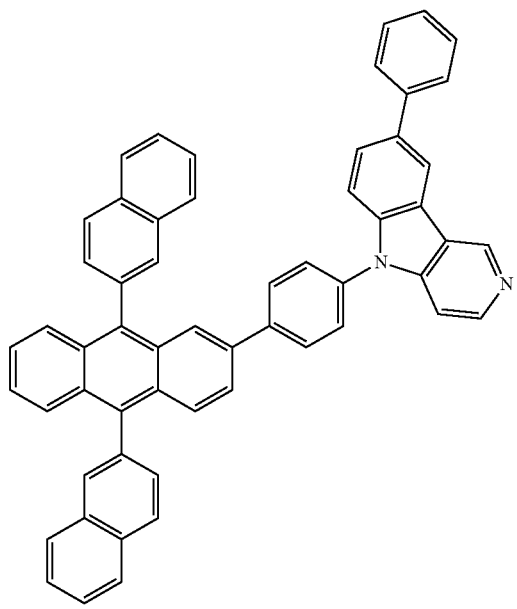

[Chem. 79]

[Compound 77]

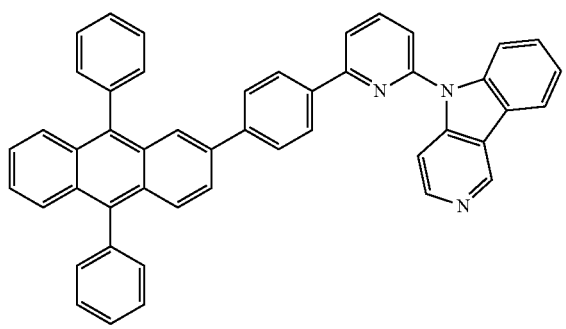

[Chem. 80]

[Compound 78]

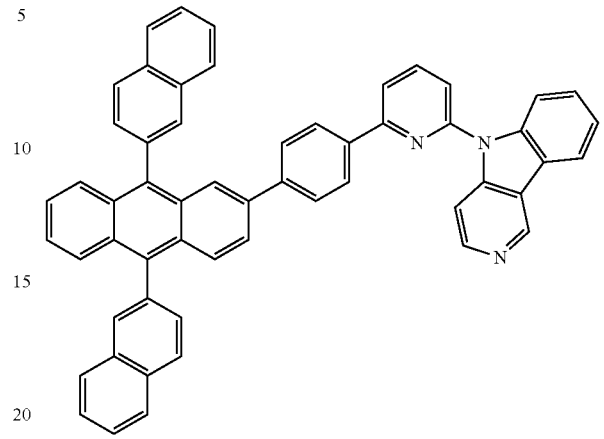

Purification of these compounds was performed by purification by column chromatography, adsorption purification with silica gel, active carbon, activated clay, or the like, a recrystallization or crystallization method with a solvent, or the like. Identification of the compounds was performed by NMR analysis. As physical properties, glass-transition temperature (Tg) and melting point measurement were carried out. The melting point serves as an indicator of vapor deposition properties, and the glass transition point (Tg) serves as an indicator of stability in a thin-film state.

The melting point and the glass transition point were measured using a powder material by means of a highly sensitive differential scanning calorimeter DSC 3100S manufactured by Bruker AXS.

Further, the work function was measured by preparing a thin film of 100 nm on an ITO substrate and using a photoelectron spectroscopy in air (Model AC-3, manufactured by Riken Keiki Co., Ltd.). The work function is regarded as an indicator of hole-blocking ability.

Examples of the structure of the organic EL device of the invention include a structure having an anode, a hole-injection layer, a hole-transport layer, a light-emitting layer, a hole-blocking layer, an electron-transport layer and a cathode in this order on a substrate, and a structure further having an electron-injection layer between the electron-transport layer and the cathode. In these multilayer structures, it is possible to omit several layers of the organic layers and, for example, the structure may have a constitution sequentially having an anode, a hole-transport layer, a light-emitting layer, an electron-transport layer and a cathode on a substrate.

As the anode of the organic EL device, an electrode material having a large work function, such as ITO or gold, is used. As the hole-injection layer, other than copper phthalocyanine (hereinafter, simply referred to as CuPc), materials such as starburst-type triphenylamine derivative and various triphenylamine tetramers, and coat-type polymer materials may be used.

For the hole-transport layer, a benzidine derivative such as N,N'-diphenyl-N,N'-di(m-tolyl)-benzidine (hereinafter, simply referred to as TPD), N,N'-diphenyl-N,N'-di(α-naphthyl)-benzidine (hereinafter, simply referred to as NPD) and N,N,N',N'-tetrabiphenylylbenzidine, various triphenylamine tetramers, and the like may be used. Also, for the hole-injection/transport layer, coat-type polymer materials such as poly(3,4-ethylenedioxythiophene) (hereinafter, simply referred to as PEDOT)/poly(styrene sulfonate) (hereinafter, simply referred to as PSS) may be used.

As for the light-emitting layer, hole-blocking layer, and electron-transport layer of the organic EL device of the present invention, other than the compound having a substituted anthracene ring structure and a pyridoindole ring structure, a compound having hole-blocking action, such as aluminum complexes, thiazole derivatives, oxazole derivatives, carbazole derivatives, polydialkylfluorene derivatives, phenanthroline derivatives such as BCP and triazole derivatives such as TAZ, may be used.

A conventional light-emitting material such as aluminum complex and styryl derivative is used for the light-emitting layer and the compound having a substituted anthracene ring structure and a pyridoindole ring structure of the present invention is used for the hole-blocking layer or electron-transport layer, whereby a high-performance organic EL device can be produced. Also, a fluorescent material such as quinacridone, coumarin and rubrene can be used as the host material of the light-emitting layer. As regards the phosphorescent material, for example, a green phosphorescent material such as phenylpyridine iridium complex Ir(ppy)3, a blue phosphorescent material such as FIrpic and Fir6, and a red phosphorescent material such as Btp2Ir(acac), are used. As regards the host material at this time, for example, a carbazole derivative such as 4,4'-di(N-carbazolyl)biphenyl (hereinafter, simply referred to as CBP), 4,4',4''-tri(N-carbazolyl)triphenylamine (hereinafter, simply referred to as TCTA) and 1,3-bis(carbazol-9-yl)benzene (hereinafter, simply referred to as mCP) may be used as a hole-injecting/transporting host material, and such as 2,2',2''-(1,3,5-phenylene)tris(1-phenyl-1H-benzimidazole) (hereinafter, simply referred to as TPBI) may be used as an electron-transporting host material, whereby a high-performance organic EL device can be produced.

Furthermore, the compound having a substituted anthracene ring structure and a pyridoindole ring structure can be used as the electron-transport layer through multilayering or co-deposition with conventional electron-transport material(s).

The organic EL device of the invention may have an electron-injection layer. As the electron-injection layer, other than the compound of the present invention, lithium fluoride or the like may be used. For the cathode, an electrode material having a low work function such as aluminum, or an alloy having a low work function such as aluminum magnesium is used as an electrode material.

Embodiments of the invention will be illustrated in greater detail with reference to the following Examples, but the invention should not be construed as being limited thereto so long as not exceeding the gist of the invention.

Example 1

Synthesis of 9,10-Diphenyl-2-(5H-pyrido[4,3-b]indol-5-yl)anthracene (Compound 3)

In a nitrogen atmosphere, 4.7 g of 2-bromo-9,10-diphenylanthracene, 2.6 g of 5H-pyrido[4,3-b]indole, 0.4 g of copper powder, 4.3 g of potassium carbonate, 0.3 ml of dimethyl sulfoxide and 30 ml of n-dodecane were added to a reaction vessel, then heated and stirred at 210° C. for 18 hours. After cooling to room temperature, 300 ml of chloroform and 30 ml of methanol were added thereto and insoluble materials were removed by filtration. The filtrate was concentrated under reduced pressure to obtain a crude product, and the crude product was purified by column chromatography (carrier: NH silica gel, eluent: toluene/chloroform) to obtain 1.7 g (yield: 30%) of 9,10-diphenyl-2-(5H-pyrido[4,3-b]indol-5-yl)anthracene (Compound 3) as a yellow powder.

The structure of the obtained yellow powder was identified using NMR. FIG. 1 shows the results of $^1$H-NMR measurement.

The following 24 hydrogen signals were detected on $^1$H-NMR (CDCl$_3$). δ (ppm)=9.35 (1H), 8.48 (1H), 8.18 (1H), 7.95 (1H), 7.85 (1H), 7.77 (2H), 7.66 (2H), 7.61-7.29 (13H), 7.36 (1H), 7.29 (1H).

Example 2

Synthesis of 9,10-Diphenyl-2-[4-(5H-pyrido[4,3-b]indol-5-yl)phenyl]anthracene (Compound 9)

In a nitrogen atmosphere, 4.7 g of 9,10-diphenylanthracene-2-boronic acid, 2.8 g of 5-(4-bromophenyl)-5H-pyrido[4,3-b]indole, 0.50 g of tetrakistriphenylphosphine palladium, 15 ml of an aqueous 2 M potassium carbonate solution, 20 ml of toluene and 1.5 ml of ethanol were added to a reaction vessel, then heated under reflux with stirring for 18 hours. After cooling to room temperature, a crude product was collected by filtration, and the crude product was purified by column chromatography (carrier: silica gel, eluent: toluene/ethyl acetate) to obtain 1.6 g (yield: 32%) of 9,10-diphenyl-2-[4-(5H-pyrido[4,3-b]indol-5-yl)phenyl]anthracene (Compound 9) as a yellow powder.

Figure 2:
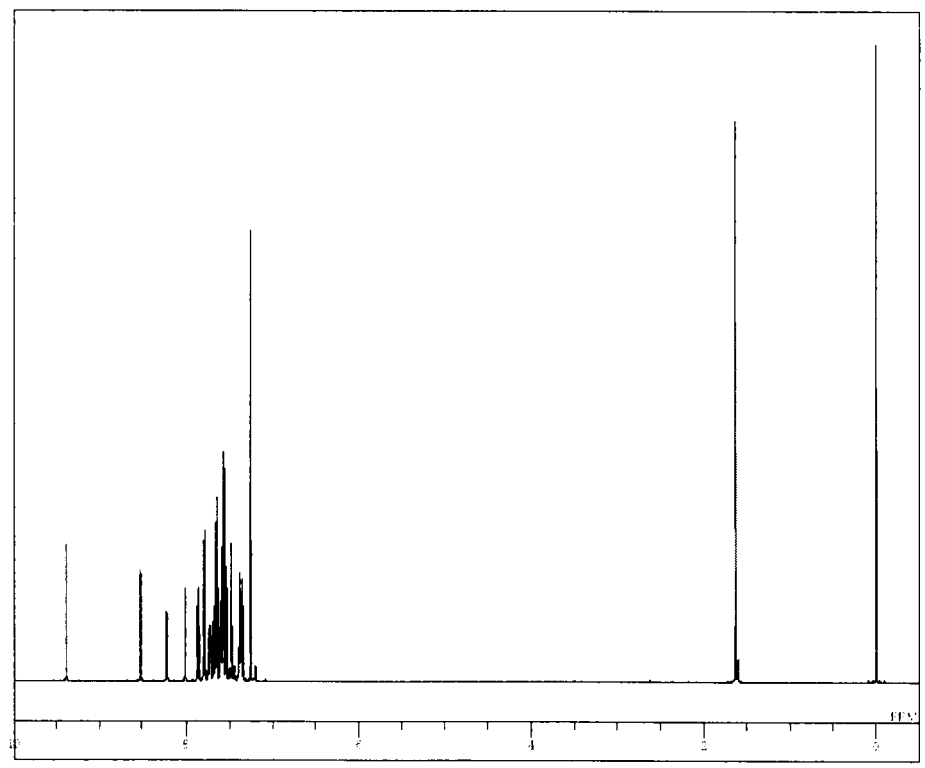
FIG. 2 is a 1H-NMR chart of the compound (Compound 9) of Invention Example 2.

The structure of the obtained yellow powder was identified using NMR. FIG. 2 shows the results of $^1$H-NMR measurement.

The following 28 hydrogen signals were detected on $^1$H-NMR (CDCl$_3$). δ (ppm)=9.39 (1H), 8.52 (1H), 8.22 (1H), 8.01 (1H), 7.86 (1H), 7.79 (2H), 7.73 (2H), 7.70-7.64 (5H), 7.61-7.53 (8H), 7.49 (2H), 7.49-7.34 (4H).

Example 3

Synthesis of 9,10-Diphenyl-2-[6-(5H-pyrido[4,3-b]indol-5-yl)pyridin-3-yl]anthracene (Compound 15)

In a nitrogen atmosphere, 4.5 g of 9,10-diphenylanthracene-2-boronic acid, 3.0 g of 5-(5-bromopyridin-2-yl)-5H-pyrido[4,3-b]indole, 0.55 g of tetrakistriphenylphosphine palladium, 19 ml of an aqueous 2 M potassium carbonate solution, 72 ml of toluene and 18 ml of ethanol were added to a reaction vessel, then heated under reflux with stirring for 18 hours. After cooling to room temperature, 100 ml of toluene and 100 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent: toluene) to obtain 3.0 g (yield: 57%) of 9,10-diphenyl-2-[6-(5H-pyrido[4,3-b]indol-5-yl)pyridin-3-yl]anthracene (Compound 15) as a yellow powder.

Figure 3:
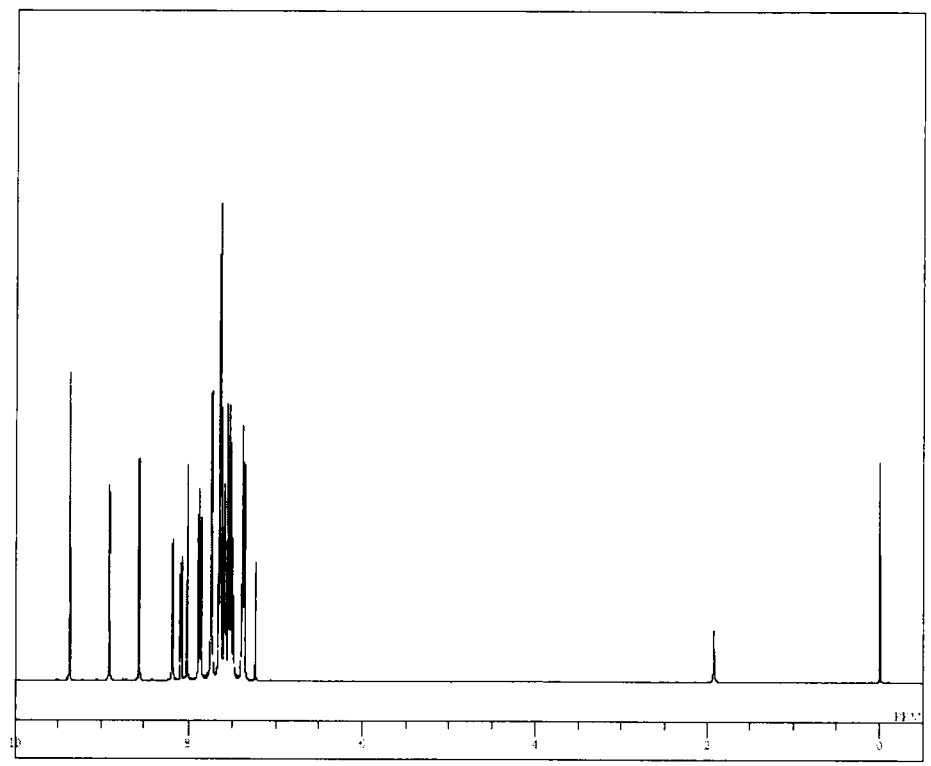
FIG. 3 is a 1H-NMR chart of the compound (Compound 15) of Invention Example 3.

The structure of the obtained yellow powder was identified using NMR. FIG. 3 shows the results of $^1$H-NMR measurement.

The following 27 hydrogen signals were detected on $^1$H-NMR (CDCl$_3$). δ (ppm)=9.37 (1H), 8.90 (1H), 8.56 (1H), 8.18 (1H), 8.06-8.10 (1H), 8.01 (1H), 7.83-7.90 (2H), 7.74 (3H), 7.47-7.68 (13H), 7.33-7.41 (3H).

Example 4

Synthesis of 9,10-Diphenyl-2-[6-(5H-pyrido[4,3-b]indol-5-yl)pyridin-2-yl]anthracene (Compound 27)

In a nitrogen atmosphere, 4.7 g of 9,10-diphenylanthracene-2-boronic acid, 2.8 g of 5-(6-bromopyridin-2-yl)-5H-pyrido[4,3-b]indole, 0.51 g of tetrakistriphenylphosphine palladium, 22 ml of an aqueous 2 M potassium carbonate solution, 72 ml of toluene and 18 ml of ethanol were added to a reaction vessel, then heated under reflux with stirring for 17 hours. After cooling to room temperature, 100 ml of toluene and 100 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent: toluene) to obtain 2.7 g (yield: 54%) of 9,10-diphenyl-2-[6-(5H-pyrido[4,3-b]indol-5-yl)pyridin-2-yl]anthracene (Compound 27) as a yellow powder.

Figure 4:
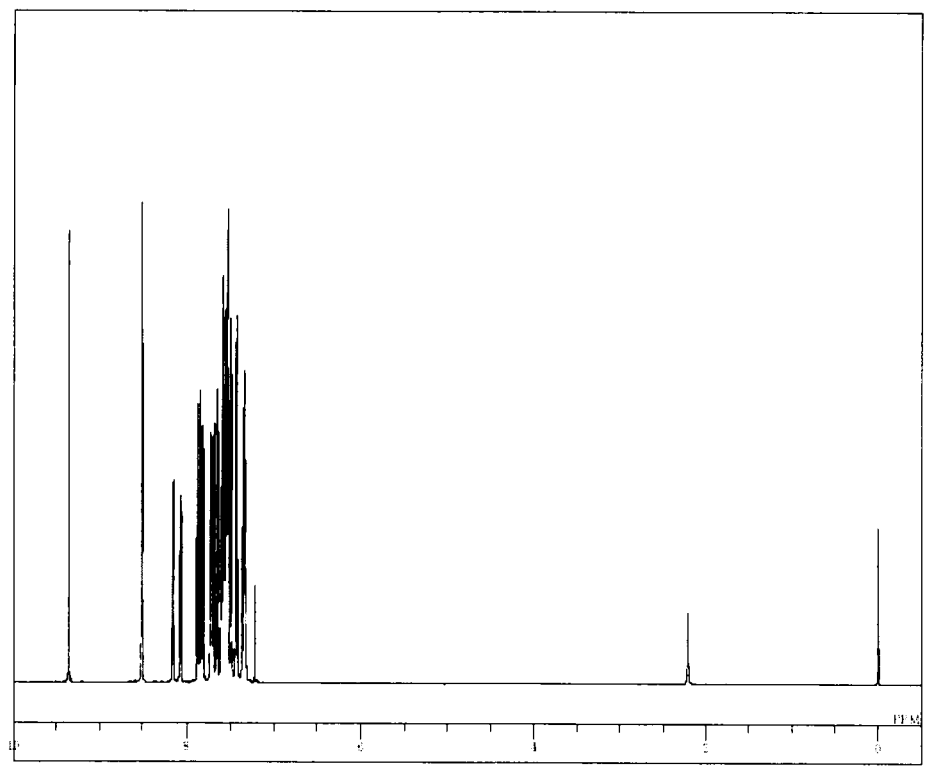
FIG. 4 is a 1H-NMR chart of the compound (Compound 27) of Invention Example 4.

The structure of the obtained yellow powder was identified using NMR. FIG. 4 shows the results of $^1$H-NMR measurement.

The following 27 hydrogen signals were detected on $^1$H-NMR (CDCl$_3$). δ (ppm)=9.37 (1H), 8.48-8.53 (2H), 8.15 (1H), 8.07 (1H), 7.78-7.89 (3H), 7.64-7.74 (4H), 7.48-7.63 (10H), 7.41-7.46 (2H), 7.30-7.38 (3H).

Example 5

Synthesis of 9,10-Di(naphthalen-2-yl)-2-(5H-pyrido[4,3-b]indol-5-yl)anthracene (Compound 6)

In a nitrogen atmosphere, 3.0 g of 2-bromo-9,10-di(naphthalen-2-yl)anthracene, 1.2 g of 5H-pyrido[4,3-b]indole, 0.2 g of copper powder, 1.7 g of potassium carbonate, 0.1 ml of dimethyl sulfoxide and 6 ml of n-dodecane were added to a reaction vessel, then heated and stirred at 210° C. for 8 hours. After cooling to room temperature, 80 ml of toluene was added thereto, followed by stirring under heating, and the insoluble materials were removed by filtration at 80° C. The filtrate was concentrated under reduced pressure to obtain a crude product, and the crude product was purified by column chromatography (carrier: NH silica gel, eluent: toluene/ethyl acetate) to obtain 1.9 g (yield: 54%) of 9,10-di(naphthalen-2-yl)-2-(5H-pyrido[4,3-b]indol-5-yl)anthracene (Compound 6) as a yellow powder.

Figure 5:
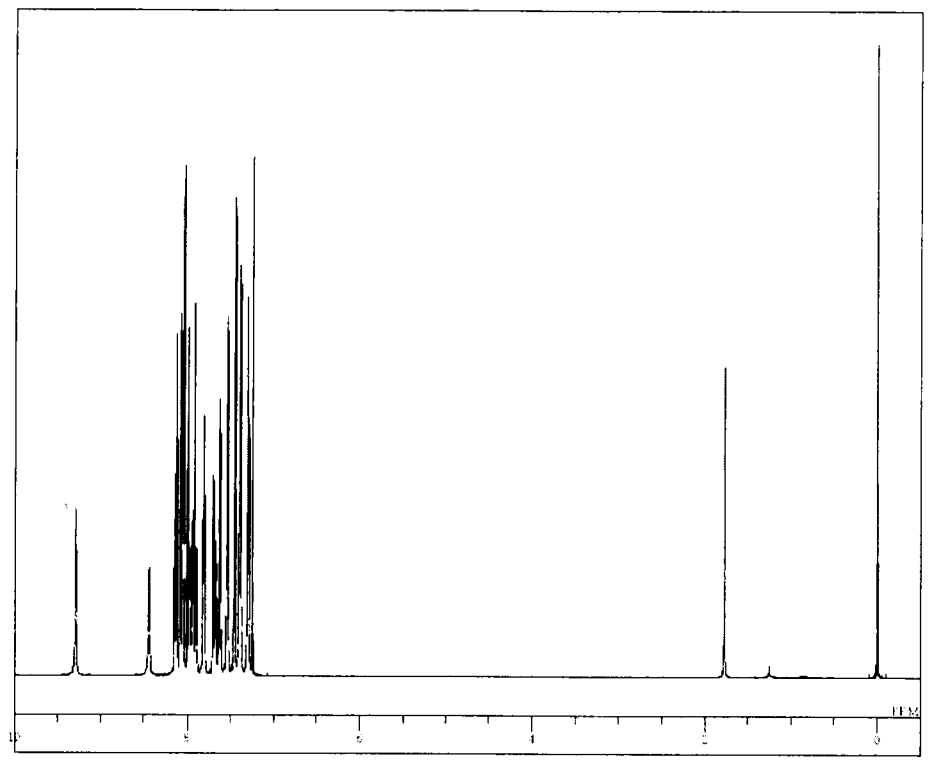
FIG. 5 is a 1H-NMR chart of the compound (Compound 6) of Invention Example 5.

The structure of the obtained yellow powder was identified using NMR. FIG. 5 shows the results of $^1$H-NMR measurement.

The following 28 hydrogen signals were detected on $^1$H-NMR (CDCl$_3$). δ (ppm)=9.30 (1H), 8.45 (1H), 8.13 (2H), 8.06 (4H), 7.89-8.00 (5H), 7.81 (2H), 7.61-7.71 (4H), 7.54 (2H), 7.46 (2H), 7.38-7.41 (3H), 7.30 (2H).

Example 6

Synthesis of 9,10-Di(naphthalen-2-yl)-2-[4-(5H-pyrido[4,3-b]indol-5-yl)phenyl]anthracene (Compound 12)

In a nitrogen atmosphere, 3.5 g of 9,10-di(naphthalen-2-yl)anthracene-2-boronic acid, 2.2 g of 5-(4-bromophenyl)-5H-pyrido[4,3-b]indole, 0.35 g of tetrakistriphenylphosphine palladium, 10 ml of an aqueous 2 M potassium carbonate solution, 40 ml of toluene and 10 ml of ethanol were added to a reaction vessel, then heated under reflux with stirring for 8 hours. After cooling to room temperature, 80 ml of toluene and 20 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent: toluene) to obtain 2.4 g (yield: 52%) of 9,10-di(naphthalen-2-yl)-2-[4-(5H-pyrido[4,3-b]indol-5-yl)phenyl]anthracene (Compound 12) as a yellow powder.

Figure 6:
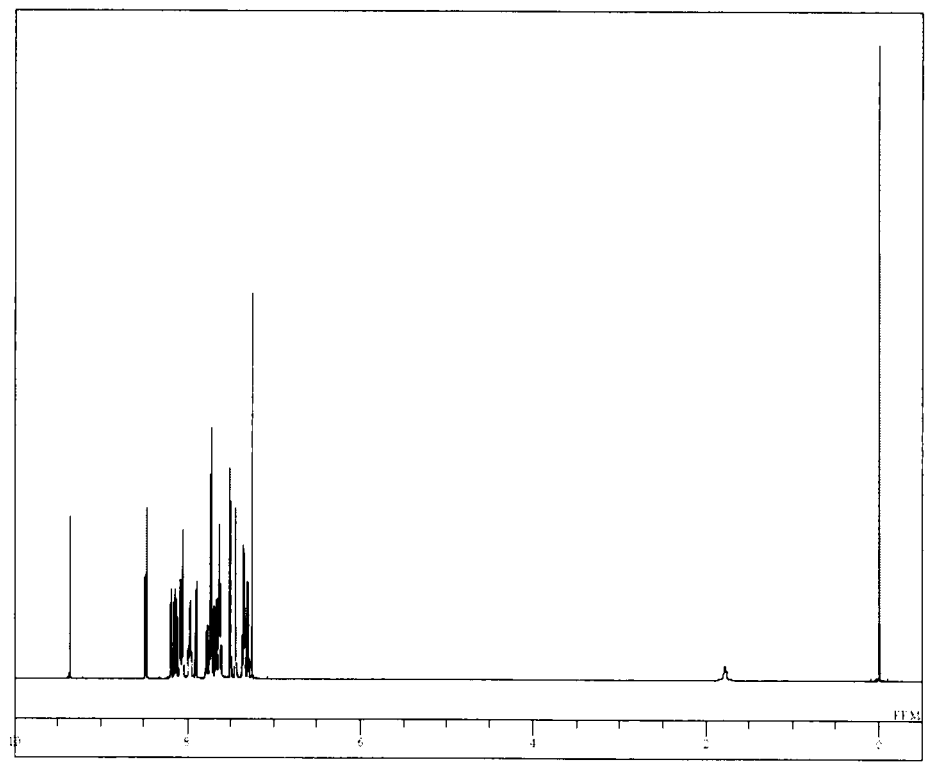
FIG. 6 is a 1H-NMR chart of the compound (Compound 12) of Invention Example 6.

The structure of the obtained yellow powder was identified using NMR. FIG. 6 shows the results of $^1$H-NMR measurement.

The following 32 hydrogen signals were detected on $^1$H-NMR (CDCl$_3$). δ (ppm)=9.36 (1H), 8.48 (1H), 8.19 (1H), 8.14 (2H), 8.05-8.08 (5H), 7.97 (2H), 7.90 (1H), 7.61-7.79 (11H), 7.51 (2H), 7.44 (2H), 7.32-7.37 (3H), 7.30 (1).

Example 7

Synthesis of 9,10-Diphenyl-2-[4'-(5H-pyrido[4,3-b]indol-5-yl)biphenyl-4-yl]anthracene (Compound 42)

In a nitrogen atmosphere, 2.8 g of 9,10-diphenylanthracene-2-boronic acid, 3.0 g of 5-(4'-bromobiphenyl-4-yl)-5H-pyrido[4,3-b]indole, 0.40 g of tetrakistriphenylphosphine palladium, 10 ml of an aqueous 2 M potassium carbonate solution, 15 ml of toluene and 2 ml of ethanol were added to a reaction vessel, then heated under reflux with stirring for 2 hours. After cooling to room temperature, 60 ml of toluene and 50 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent: toluene/ethyl acetate) to obtain 3.0 g (yield: 62%) of 9,10-diphenyl-2-[4'-(5H-pyrido[4,3-b]indol-5-yl)biphenyl-4-yl]anthracene (Compound 42) as a yellow powder.

Figure 7:
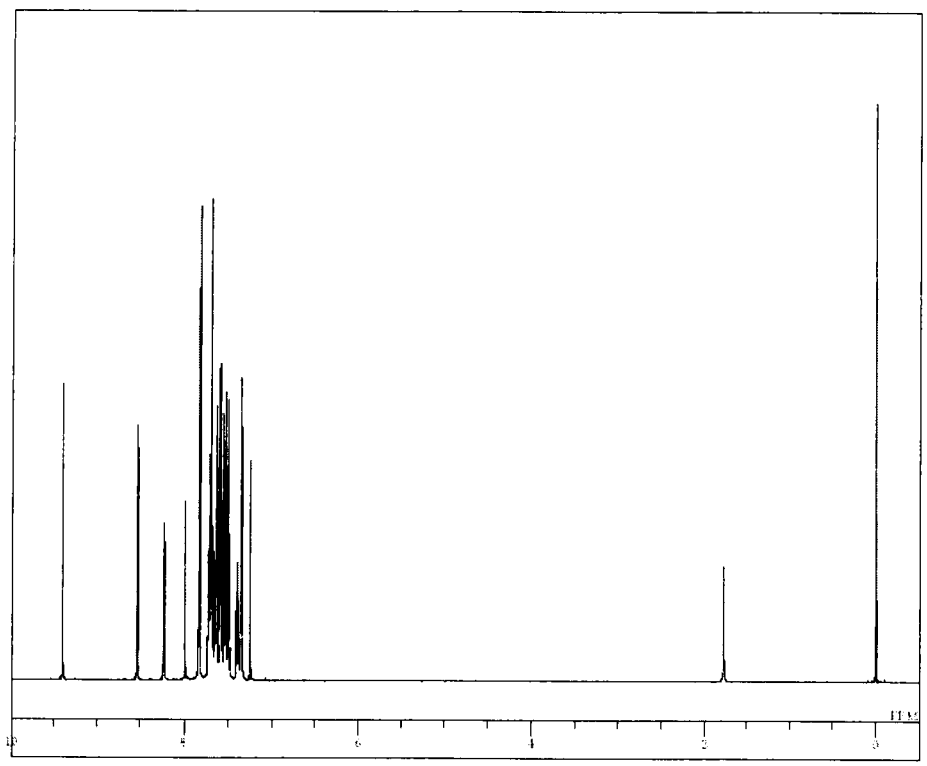
FIG. 7 is a 1H-NMR chart of the compound (Compound 42) of Invention Example 7.

The structure of the obtained yellow powder was identified using NMR. FIG. 7 shows the results of $^1$H-NMR measurement.

The following 32 hydrogen signals were detected on $^1$H-NMR (CDCl$_3$). δ (ppm)=9.40 (1H), 8.54 (1H), 8.23 (1H), 7.99 (1H), 7.83 (3H), 7.48-7.72 (21H), 7.39 (1H), 7.35 (3H).

Example 8

Synthesis of 9,10-Di(naphthalen-2-yl)-2-[4'-(5H-pyrido[4,3-b]indol-5-yl)biphenyl-4-yl]anthracene (Compound 43)

In a nitrogen atmosphere, 2.0 g of 9,10-di(naphthalen-2-yl)anthracene-2-boronic acid, 1.5 g of 5-(4'-bromobiphenyl-4-yl)-5H-pyrido[4,3-b]indole, 0.20 g of tetrakistriphenylphosphine palladium, 6 ml of an aqueous 2 M potassium carbonate solution, 23 ml of toluene and 6 ml of ethanol were added to a reaction vessel, then heated under reflux with stirring for 5 hours. After cooling to room temperature, 50 ml of toluene and 20 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent: toluene/ethyl acetate) to obtain 1.8 g (yield: 63%) of 9,10-di(naphthalen- 2-yl)-2-[4'-(5H-pyrido[4,3-b]indol-5-yl)biphenyl-4-yl]anthracene (Compound 43) as a yellow powder.

Figure 8:
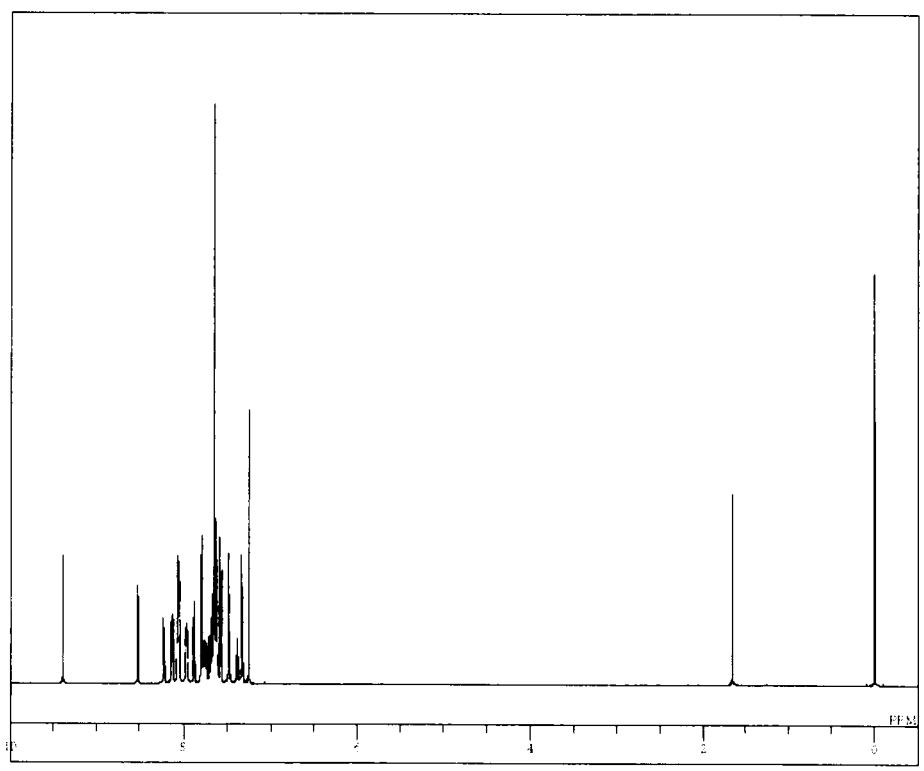
FIG. 8 is a 1H-NMR chart of the compound (Compound 43) of Invention Example 8.

The structure of the obtained yellow powder was identified using NMR. FIG. 8 shows the results of $^1$H-NMR measurement.

The following 36 hydrogen signals were detected on $^1$H-NMR (CDCl$_3$). δ (ppm)=9.39 (1H), 8.52 (1H), 8.22 (1H), 8.13 (2H), 8.04-8.07 (5H), 7.97 (2H), 7.87 (1H), 7.57-7.80 (17H), 7.48 (2H), 7.38 (1H), 7.33 (3H).

Example 9

Synthesis of 9,10-Diphenyl-2-[5-(5H-pyrido[4,3-b]indol-5-yl)pyridin-3-yl]anthracene (Compound 73)

In a nitrogen atmosphere, 3.2 g of 9,10-diphenylanthracene-2-boronic acid, 2.4 g of 5-(5-bromopyridin-3-yl)-5H-pyrido[4,3-b]indole, 0.44 g of tetrakistriphenylphosphine palladium, 11 ml of an aqueous 2 M potassium carbonate solution, 15 ml of toluene and 2 ml of ethanol were added to a reaction vessel, then heated under reflux with stirring for 2 hours. After cooling to room temperature, 30 ml of toluene and 20 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent: toluene/ethyl acetate) to obtain 2.2 g (yield: 52%) of 9,10-diphenyl-2-[5-(5H-pyrido[4,3-b]indol-5-yl)pyridin-3-yl]anthracene (Compound 73) as a yellow powder.

Figure 9:
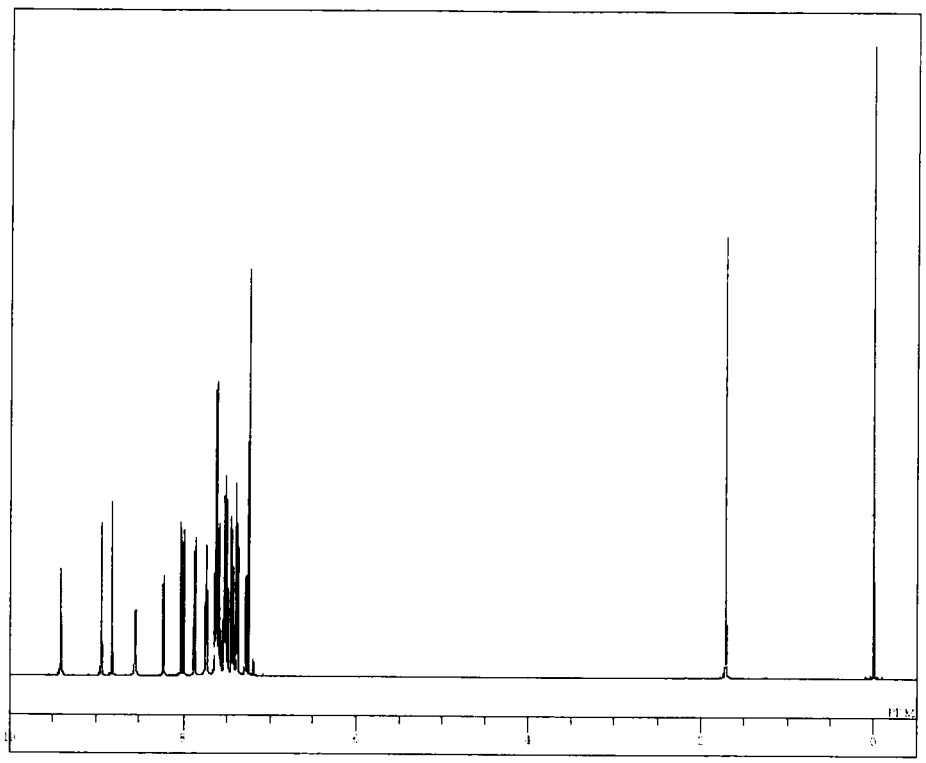
FIG. 9 is a 1H-NMR chart of the compound (Compound 73) of Invention Example 9.

The structure of the obtained yellow powder was identified using NMR. FIG. 9 shows the results of $^1$H-NMR measurement.

The following 27 hydrogen signals were detected on $^1$H-NMR (CDCl$_3$). δ (ppm)=9.41 (1H), 8.94 (1H), 8.82 (1H), 8.55 (1H), 8.23 (1H), 8.03 (1H), 8.00 (1H), 7.87 (1H), 7.74 (2H), 7.57-7.65 (7H), 7.49-7.54 (5H), 7.37-7.45 (4H), 7.29 (1H).

Example 10

Synthesis of 9,10-Di(naphthalen-2-yl)-2-[6-(5H-pyrido[4,3-b]indol-5-yl)pyridin-2-yl]anthracene (Compound 30)

In a nitrogen atmosphere, 3.5 g of 9,10-di(naphthalen-2-yl)anthracene-2-boronic acid, 2.2 g of 5-(6-bromopyridin-2-yl)-5H-pyrido[4,3-b]indole, 0.35 g of tetrakistriphenylphosphine palladium, 10 ml of an aqueous 2 M potassium carbonate solution, 40 ml of toluene and 10 ml of ethanol were added to a reaction vessel, then heated under reflux with stirring for 5 hours. After cooling to room temperature, 100 ml of toluene and 100 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent:toluene) to obtain 2.2 g (yield: 48%) of 9,10-di(naphthalen-2-yl)-2-(6-(5H-pyrido[4,3-b]indol-5-yl)pyridin-2-yl]anthracene (Compound 30) as a yellow powder.

Figure 10:
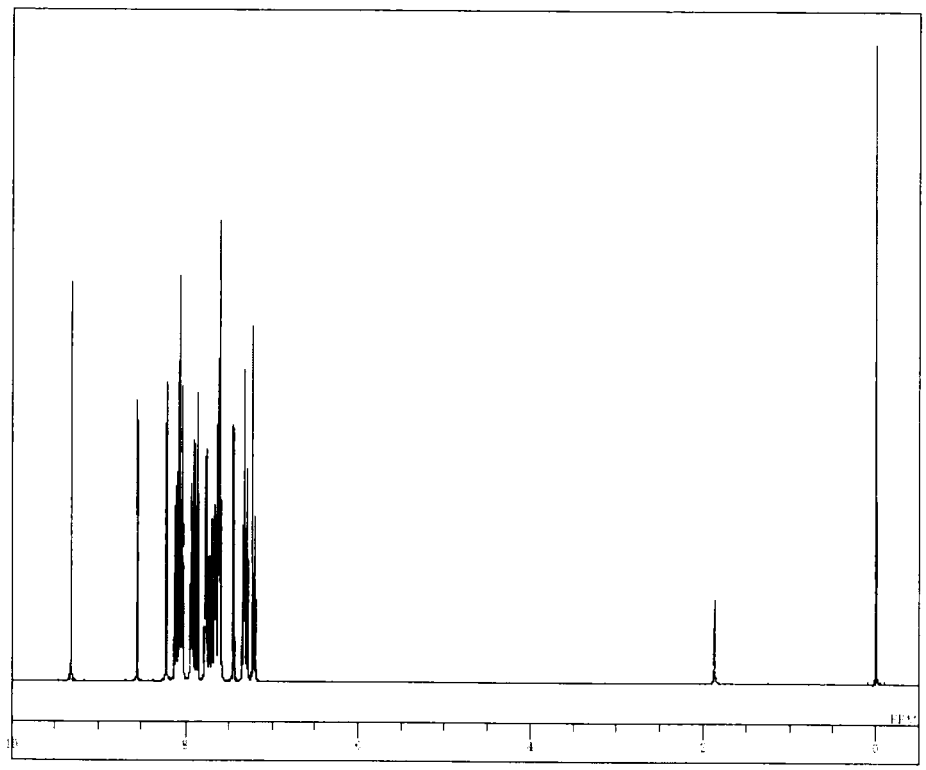
FIG. 10 is a 1H-NMR chart of the compound (Compound 30) of Invention Example 10.

The structure of the obtained yellow powder was identified using NMR. FIG. 10 shows the results of $^1$H-NMR measurement.

The following 31 hydrogen signals were detected on $^1$H-NMR (CDCl$_3$). δ (ppm)=9.32 (1H), 8.55 (1H), 8.22 (1H), 8.03-8.13 (8H), 7.85-7.95 (4H), 7.58-7.78 (11H), 7.44 (1H), 7.28-7.35 (3H), 7.21 (1H).

Example 11

Synthesis of 9,10-Diphenyl-2-[4-(8-phenyl-5H-pyrido[4,3-b]indol-5-yl)phenyl]anthracene (Compound 75)

In a nitrogen atmosphere, 2.8 g of 9,10-diphenylanthracene-2-boronic acid, 2.4 g of 5-(4-bromophenyl)-8-phenyl-5H-pyrido[4,3-b]indole, 0.21 g of tetrakistriphenylphosphine palladium, 16 ml of an aqueous 2 M potassium carbonate solution, 40 ml of toluene and 10 ml of ethanol were added to a reaction vessel, then heated under reflux with stirring for 4 hours. After cooling to room temperature, 100 ml of toluene and 100 ml of water were added thereto, followed by stirring, and the organic layer was separated by liquid separation. The organic layer was dried over magnesium sulfate, and then concentrated under reduced pressure to obtain a crude product. The crude product was purified by column chromatography (carrier: NH silica gel, eluent: toluene/ethyl acetate) to obtain 2.7 g (yield: 69%) of 9,10-diphenyl-2-[4-(8-phenyl-5H-pyrido[4,3-b]indol-5-yl)phenyl]anthracene (Compound 75) as a yellow powder.

Figure 11:
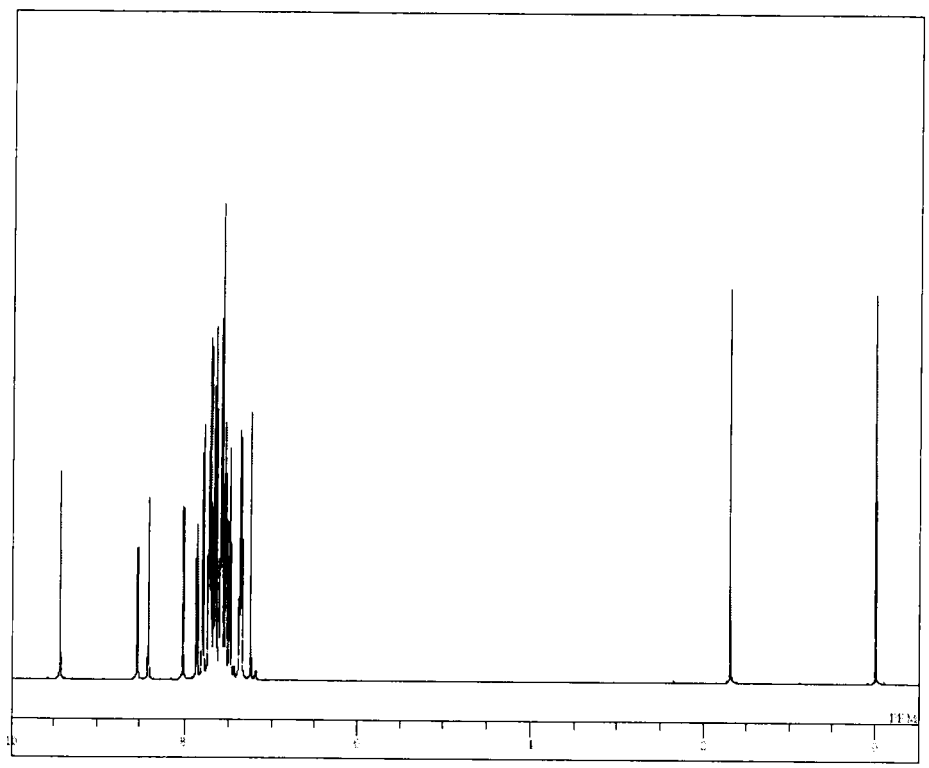
FIG. 11 is a 1H-NMR chart of the compound (Compound 75) of Invention Example 11.

The structure of the obtained yellow powder was identified using NMR. FIG. 11 shows the results of $^1$H-NMR measurement.

The following 32 hydrogen signals were detected on $^1$H-NMR (CDCl$_3$). δ (ppm)=9.43 (1H), 8.53 (1H), 8.41 (1H), 8.02 (1H), 7.86 (1H), 7.79 (2H), 7.63-7.74 (10H), 7.53-7.61 (9H), 7.49 (2H), 7.34-7.38 (4H).

Example 12

With respect to the compounds of the present invention, the melting point and glass transition point were measured by a high-sensitivity differential scanning calorimeter (DSC 3100S, manufactured by Bruker AXS K.K.).

|  | Melting Point | Glass Transition Point |
|---|---|---|
| Compound of Invention Example 1 | 269° C. | 130° C. |
| Compound of Invention Example 2 | 323° C. | 153° C. |
| Compound of Invention Example 3 | 311° C. | 148° C. |
| Compound of Invention Example 4 | 176° C. | 138° C. |
| Compound of Invention Example 5 | 320° C. | 170° C. |
| Compound of Invention Example 6 | 342° C. | 186° C. |
| Compound of Invention Example 7 | 283° C. | 161° C. |
| Compound of Invention Example 8 | 363° C. | 190° C. |
| Compound of Invention Example 9 | 240° C. | 140° C. |
| Compound of Invention Example 10 | 295° C. | 168° C. |

The compounds of the present invention have a glass transition point of 100° C. or more, and this reveals that the compounds of the present invention are stable in the thin-film state.

Example 13

Using each of the compounds of the present invention, a deposited film having a film thickness of 100 nm was formed on an ITO substrate and measured for the work function by means of an atmospheric photoelectron spectrometer (Model AC-3, manufactured by Riken Keiki Co., Ltd.).

|  | Work Function |
|---|---|
| Compound of Invention Example 1 | 6.24 eV |
| Compound of Invention Example 2 | 5.88 eV |
| Compound of Invention Example 3 | 5.80 eV |
| Compound of Invention Example 4 | 5.90 eV |
| Compound of Invention Example 5 | 5.83 eV |
| Compound of Invention Example 6 | 5.79 eV |
| Compound of Invention Example 7 | 5.80 eV |
| Compound of Invention Example 8 | 5.73 eV |
| Compound of Invention Example 9 | 5.85 eV |
| Compound of Invention Example 10 | 5.83 eV |

As seen above, the compounds of the present invention have a value larger than is a work function of 5.4 eV possessed by a general hole-transport material such as NPD and TPD, and have a high hole-blocking ability.

Example 14

Figure 12:
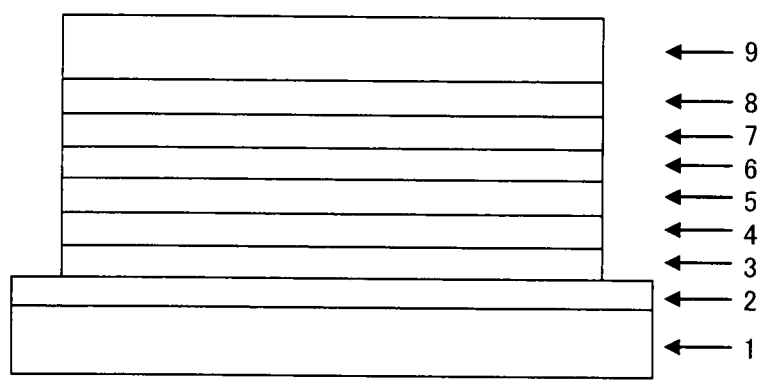
FIG. 12 is a drawing showing the constitution of the EL devices of Examples 14 to 22.
Figure 13:
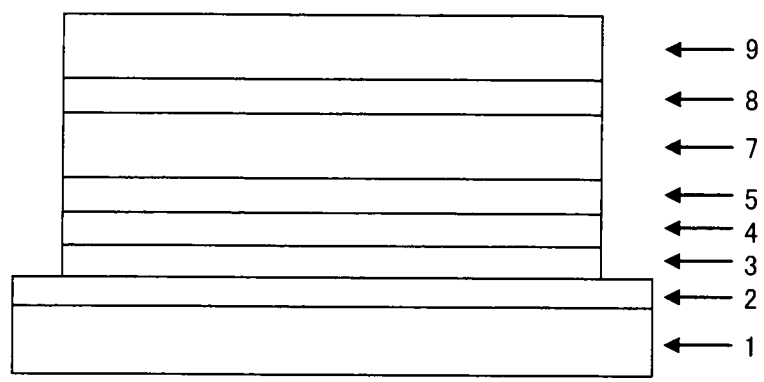
FIG. 13 is a drawing showing the constitution of the EL device of Comparative Example 1.

An organic EL device was produced, as shown in FIG. 12, by sequentially depositing a hole-injection layer 3, a hole-transport layer 4, a light-emitting layer 5, a hole-blocking layer 6, an electron-transport layer 7, an electron-injection layer 8, and a cathode (aluminum electrode) 9 on a glass substrate 1 having previously formed thereon an ITO electrode as a transparent electrode 2.

Specifically, the glass substrate 1 having ITO formed thereon to a film thickness of 150 nm was washed with an organic solvent, and the surface was then washed by an oxygen plasma treatment. Thereafter, the glass substrate with an ITO electrode was fixed in a vacuum deposition device, and the pressure therein was reduced to 0.001 Pa or less. Subsequently, Compound 79 having a structural formula shown below was formed thereon as the hole-injection layer 3 to cover the transparent electrode 2 at a deposition rate of 1.0 Å/sec to a film thickness of 20 nm. On the hole-injection layer 3, Compound 80 having a structural formula shown below was formed as the hole-transport layer 4 at a deposition rate of 1.0 Å/sec to a film thickness of 40 nm. On the hole-transport layer 4, Compound 81 having a structural formula shown below and Compound 82 having a structural formula shown below were formed as the light-emitting layer 5 to a film thickness of 30 nm by performing binary deposition at deposition rates giving a deposition rate ratio of Compound 81:Compound 82=5:95 (Compound 81: 1.52 Å/sec, Compound 82: 0.08 Å/sec). On the light-emitting layer 5, the compound of invention Example 1 (Compound 3) was formed as the hole-blocking layer-cum-electron-transport layer 6 and 7 at a deposition rate of 1.0 Å/sec to a film thickness of 30 nm. On the hole-blocking layer-cum-electron-transport layer 6 and 7, lithium fluoride was formed as the electron-injection layer 8 at a deposition rate of 0.1 Å/sec to a film thickness of 0.5 nm. Finally, aluminum was deposited to a film thickness of 150 nm to form the cathode 9. The produced organic EL device was subjected to measurement of characteristic properties at ordinary temperature in the atmosphere.

The measurement results of light emitting characteristics when applying a direct voltage to the organic EL device produced using the compound of invention Example 1 (Compound 3) are shown together in Table 1.

[Chem. 81]

[Compound 79]

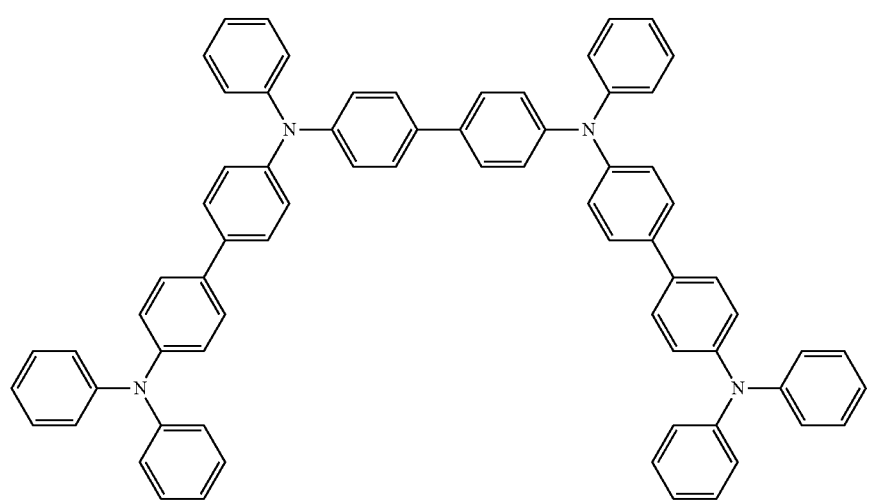

[Chem. 82]

[Compound 80]

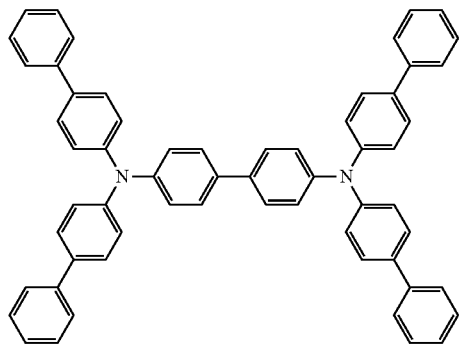

[Chem. 83]

[Compound 81]

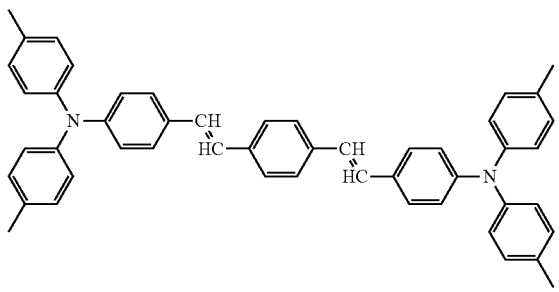

[Chem. 84]

[Compound 82]

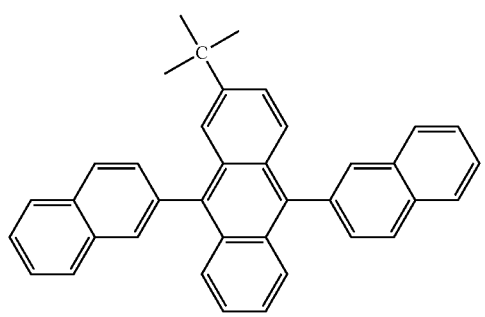

Example 15

An organic EL device was produced by the same method as in Example 14 except for depositing the compound of invention Example 2 (Compound 9) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

Example 16

An organic EL device was produced by the same method as in Example 14 except for depositing the compound of invention Example 3 (Compound 15) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

Example 17

An organic EL device was produced by the same method as in Example 14 except for depositing the compound of invention Example 4 (Compound 27) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

Example 18

An organic EL device was produced by the same method as in Example 14 except for depositing the compound of invention Example 5 (Compound 6) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

Example 19

An organic EL device was produced by the same method as in Example 14 except for depositing the compound of invention Example 6 (Compound 12) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

Example 20

An organic EL device was produced by the same method as in Example 14 except for depositing the compound of invention Example 7 (Compound 42) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

Example 21

An organic EL device was produced by the same method as in Example 14 except for depositing the compound of invention Example 8 (Compound 43) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

Example 22

An organic EL device was produced by the same method as in Example 14 except for depositing the compound of invention Example 9 (Compound 73) to a film thickness of 30 nm as the hole-blocking layer-cum-electron-transport layer 6 and 7 in place of the compound of invention Example 1 (Compound 3). The produced organic EL device was subjected to measurement of characteristic properties at ordinary temperature in the atmosphere.

The measurement results of light emitting characteristics when applying a direct voltage to the organic EL device produced are shown together in Table 1.

COMPARATIVE EXAMPLE 1

For comparison, the material of the hole-blocking layer-cum-electron-transport layer 6 and 7 in Example 14 was replaced with $Alq_3$, and an organic EL device was produced under the same conditions as in Example 14. The produced organic EL device was subjected to measurement of characteristic properties at ordinary temperature in the atmosphere.

The measurement results of light emitting characteristics when applying a direct voltage to the organic EL device produced are shown together in Table 1.

TABLE 1

|  | Compound | Voltage [V] (@10 mA/cm$^2$) | Luminance [cd/m$^2$] (@10 mA/cm$^2$) | Luminous Efficiency [cd/A] (@10 mA/cm$^2$) | Power Efficiency [lm/W] (@10 mA/cm$^2$) |
|---|---|---|---|---|---|
| Example 14 | Compound 3 | 5.10 | 850 | 8.55 | 5.20 |
| Example 15 | Compound 9 | 4.15 | 982 | 9.82 | 7.48 |
| Example 16 | Compound 15 | 4.80 | 844 | 8.42 | 5.50 |
| Example 17 | Compound 27 | 4.00 | 932 | 9.30 | 7.32 |
| Example 18 | Compound 6 | 5.33 | 920 | 9.20 | 5.43 |
| Example 19 | Compound 12 | 4.69 | 968 | 9.68 | 6.49 |
| Example 20 | Compound 42 | 3.95 | 900 | 9.00 | 7.16 |
| Example 21 | Compound 43 | 4.15 | 1047 | 10.47 | 7.92 |
| Example 22 | Compound 73 | 5.48 | 919 | 9.19 | 5.26 |
| Comparative Example 1 | $Alq_3$ | 5.80 | 820 | 8.25 | 4.40 |

As shown in Table 1, the driving voltage at a current density of 10 mA/cm$^2$ was 5.80 V of $Alq_3$, whereas in all of Examples 14 to 22, the driving voltages were as low as from 3.95 to 5.48 V, and moreover, all of luminance, luminous efficiency and power efficiency at a current density of 10 mA/cm$^2$ were enhanced.

The emission initiation voltages were measured using the same organic EL devices as above, and the results are shown below.

|  |  | Voltage [V] |
|---|---|---|
| Example 14 | Compound 3 | 3.0 |
| Example 15 | Compound 9 | 2.9 |
| Example 16 | Compound 15 | 2.9 |
| Example 17 | Compound 27 | 2.8 |
| Example 18 | Compound 6 | 3.0 |
| Example 19 | Compound 12 | 2.9 |
| Example 20 | Compound 42 | 2.8 |
| Example 21 | Compound 43 | 2.8 |
| Example 22 | Compound 73 | 3.1 |
| Comparative Example 1 | $Alq_3$ | 3.2 |

As a result, in comparison with Comparative Example 1 using $Alq_3$, the emission initiation voltage was lowered in Examples 14-22.

As shown above, it could be found that the organic EL device of the invention has an excellent luminous efficiency and a power efficiency, and also achieves a remarkable reduction in the practical driving voltage as compared with a devices using Alq3 used as a general electron-transporting material.

While the invention has been described in detail and with reference to specific embodiments thereof, it will be apparent to one skilled in the art that various changes and modifications can be made therein without departing from the spirit and scope thereof.

This application is based on Japanese Patent Application No. 2008-243937 which was filed on Sep. 24, 2008, and the contents thereof are incorporated herein by reference.

INDUSTRIAL APPLICABILITY

Since the compound having a substituted anthracene ring structure and a pyridoindole ring structure according to the invention exhibits a good electron-injection property and an excellent hole-blocking ability, and is stable in a thin-film state, it is excellent as a compound for use in organic EL devices. By producing an organic EL device using the compound, high efficiencies can be obtained and a reduction in practical driving voltage and an improvement in durability can be attained. It becomes possible to spread the compound onto applications of, for example, electric home appliances and illuminations.

DESCRIPTION OF REFERENCE NUMERALS AND SIGNS

1: Glass substrate
2: Transparent electrode
3: Hole-injection layer
4: Hole-transport layer
5: Light-Emitting layer
6: Hole-blocking layer
7: Electron-transport layer
8: Electron-injection layer
9: Cathode

The invention claimed is:

1. A compound having a substituted anthracene ring structure and a pyridoindole ring structure, represented by the following general formula (1):

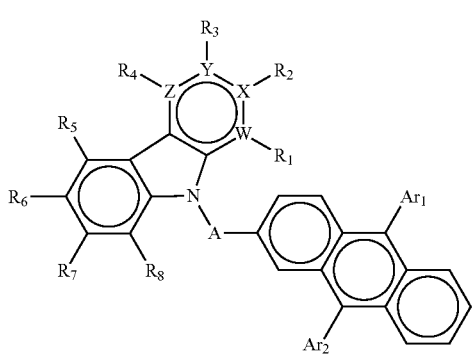

wherein $Ar_1$ and $Ar_2$ may be the same or different from each other and each represents a substituted or unsubstituted aromatic hydrocarbon group, $R_1$ to $R_8$ may be the same or different and each represents a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, a substituted or unsubstituted aromatic heterocyclic group, or a substituted or unsubstituted condensed polycyclic aromatic group, W, X, Y and Z each represents a carbon atom or a nitrogen atom, and A represents a single bond, a phenylene group, a biphenylene group, or a divalent group represented by the following general formula (A2), provided that only one of W, X, Y and Z is a nitrogen atom and the nitrogen atom does not have a substituent $R_1$ to $R_4$:

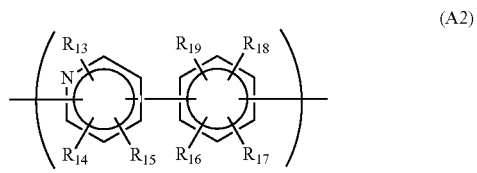

wherein $R_{13}$ to $R_{19}$ may be the same or different and each represents a hydrogen atom, a fluorine atom, a chlorine atom, a cyano group, a trifluoromethyl group, a linear or branched alkyl group having 1 to 6 carbon atoms, a substituted or unsubstituted aromatic hydrocarbon group, or a substituted or unsubstituted aromatic heterocyclic group.

2. An organic electroluminescence device comprising a pair of electrodes and at least one organic layer interposed between the electrodes, wherein said at least one organic layer contains the compound having a substituted anthracene ring structure and a pyridoindole ring structure claimed in claim 1.

3. The organic electroluminescence device as claimed in claim 2, wherein said at least one organic layer contains an electron-transport layer and the compound represented by general formula (1) is present in said electron-transport layer.

4. The organic electroluminescence device as claimed in claim 2, wherein said at least one organic layer contains a hole-blocking layer and the compound represented by general formula (1) is present in said hole-blocking layer.

5. The organic electroluminescence device as claimed in claim 2, wherein said at least one organic layer contains a light-emitting layer and the compound represented by general formula (1) is present in said light-emitting layer.

6. The organic electroluminescence device as claimed in claim 2, wherein said at least one organic layer contains an electron-injection layer and the compound represented by general formula (1) is present in said electron-injection layer.

7. The compound as claimed in claim 1, wherein:
$Ar_1$ or $Ar_2$ in general formula (1) is a phenyl group, a biphenylyl group, a terphenylyl group, a naphthyl group, an anthryl group and a phenanthryl group; and
the substituent in said substituted aromatic hydrocarbon group represented by $Ar_1$ or $Ar_2$ in general formula (1) is a fluorine atom, a chlorine atom, a cyano group, a hydroxyl group, a nitro group, a linear or branched alkyl group having 1 to 6 carbon atoms, a cyclopentyl group, a cyclohexyl group, a linear or branched alkoxy group having 1 to 6 carbon atoms, a dialkylamino group substituted with a linear or branched alkyl group having 1 to 6 carbon atoms, a phenyl group, a naphthyl group, an anthryl group, a styryl group, a pyridyl group, a pyridoindolyl group, a quinolyl group or a benzothiazolyl group.

8. The device as claimed in claim 2, wherein:
$Ar_1$ or $Ar_2$ in general formula (1) is a phenyl group, a biphenylyl group, a terphenylyl group, a naphthyl group, an anthryl group and a phenanthryl group; and
the substituent in said substituted aromatic hydrocarbon group represented by $Ar_1$ or $Ar_2$ in general formula (1) is a fluorine atom, a chlorine atom, a cyano group, a hydroxyl group, a nitro group, a linear or branched alkyl group having 1 to 6 carbon atoms, a cyclopentyl group, a cyclohexyl group, a linear or branched alkoxy group having 1 to 6 carbon atoms, a dialkylamino group substituted with a linear or branched alkyl group having 1 to 6 carbon atoms, a phenyl group, a naphthyl group, an anthryl group, a styryl group, a pyridyl group, a pyridoindolyl group, a quinolyl group or a benzothiazolyl group.

* * * * *